(12) United States Patent
Zuideveld et al.

(10) Patent No.: US 9,701,773 B2
(45) Date of Patent: Jul. 11, 2017

(54) CATALYST SYSTEM FOR POLYMERISATION OF AN OLEFIN

(71) Applicants: SAUDI BASIC INDUSTRIES CORPORATION, Riyadh (SA); SABIC GLOBAL TECHNOLOGIES B.V., Bergen op Zoom (NL)

(72) Inventors: Martin Alexander Zuideveld, Kelmis (BE); Jaiprakash Brijlal Sainani, Gujarat (IN); Vimalkumar Mahendrabhai Patel, Vadodara (IN)

(73) Assignees: SABIC GLOBAL TECHNOLOGIES, B.V., Bergen op Zoom (NL); SAUDI BASIC INDUSTRIES CORPORATION, Riyadh (SA)

(*) Notice: Subject to any disclaimer, the term of this patent is extended or adjusted under 35 U.S.C. 154(b) by 0 days.

(21) Appl. No.: 14/911,028

(22) PCT Filed: Aug. 11, 2014

(86) PCT No.: PCT/EP2014/067184
§ 371 (c)(1),
(2) Date: Feb. 9, 2016

(87) PCT Pub. No.: WO2015/022298
PCT Pub. Date: Feb. 19, 2015

(65) Prior Publication Data
US 2016/0176998 A1    Jun. 23, 2016

(30) Foreign Application Priority Data
Aug. 12, 2013  (EP) ..................... 13180041
Dec. 20, 2013  (EP) ..................... 13199154

(51) Int. Cl.
C08F 210/16    (2006.01)
C07F 7/02      (2006.01)

(52) U.S. Cl.
CPC ............ *C08F 210/16* (2013.01); *C07F 7/025* (2013.01)

(58) Field of Classification Search
None
See application file for complete search history.

(56) References Cited

U.S. PATENT DOCUMENTS

| | | |
|---|---|---|
| 4,399,054 A | 8/1983 | Ferraris et al. |
| 4,414,132 A | 11/1983 | Goodall et al. |
| 4,472,524 A | 9/1984 | Albizzati |
| 4,771,024 A | 9/1988 | Nestlerode et al. |
| 4,866,022 A | 9/1989 | Arzoumanidis et al. |
| 4,978,648 A | 12/1990 | Barbe et al. |
| 5,077,357 A | 12/1991 | Job |
| 5,093,415 A | 3/1992 | Brady, III et al. |
| 5,106,806 A | 4/1992 | Job |
| 5,556,820 A | 9/1996 | Funabashi et al. |
| 6,114,481 A | 9/2000 | McMeeking et al. |

(Continued)

FOREIGN PATENT DOCUMENTS

| | | |
|---|---|---|
| EP | 0019330 A1 | 11/1980 |
| EP | 0214708 A2 | 3/1987 |

(Continued)

OTHER PUBLICATIONS

Alcock, N. et al. "Diphenyl ketimine derivatives as a probe for Group IV pπ—dπ bonding: the structures of M(NCPh2)4 (M = Si, Ge, Sn)", Journal of the Chemical Society, Chemical Communications, 1975, Issue 5, pp. 183-184.

(Continued)

*Primary Examiner* — Catherine S Branch
(74) *Attorney, Agent, or Firm* — Cantor Colburn LLP

(57) ABSTRACT

The present invention relates to a catalyst system comprising a procatalyst, a co-catalyst and an external electron donor, wherein the external electron donor comprises a compound having the structure according to Formula I: $Si(L)_n(OR^{11})_{4-n}$ (Formula I), wherein, Si is a silicon atom with valency 4+; O is an oxygen atom with valency 2− and O is bonded to Si via the silicon-oxygen bond; n is 1, 2, 3 or 4; $R^{11}$ is a selected from the group consisting of linear, branched and cyclic alkyl having at most 20 carbon atoms and aromatic substituted and unsubstituted hydrocarbyl having 6 to 20 carbon atoms; L is a group represented by (Formula II), wherein, L is bonded to the silicon atom via the nitrogen-silicon bond; L has a single substituent on the nitrogen atom, where this single substituent is an imine carbon atom; and X and Y are independently selected from the group consisting of a hydrogen atom; a heteroatom selected from group 13, 14, 15, 16 or 17 of the IUPAC Periodic Table of the Elements; a linear, branched and cyclic alkyl having at most 20 carbon atoms, optionally containing a heteroatom selected from group 13, 14, 15, 16 or 17 of the IUPAC Periodic Table of the Elements and an aromatic substituted and unsubstituted hydrocarbyl having 6 to 20 carbon atoms, optionally containing a heteroatom selected from group 13, 14, 15, 16 or 7 of the IUPAC Periodic Table of the Elements.

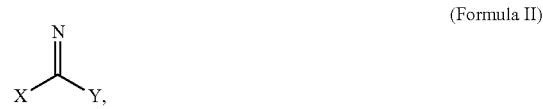

10 Claims, No Drawings

(56) References Cited

U.S. PATENT DOCUMENTS

| | | | |
|---|---|---|---|
| 6,395,670 | B1 | 5/2002 | Morini et al. |
| 6,799,568 | B2 | 10/2004 | Zakharov et al. |
| 6,825,146 | B2 | 11/2004 | Kilty et al. |
| 7,947,788 | B2 | 5/2011 | Ramjoie et al. |
| 7,956,140 | B2 | 6/2011 | Ijpeij et al. |
| 2005/0032991 | A1 | 2/2005 | Chosa et al. |
| 2010/0130709 | A1 | 5/2010 | Chen et al. |
| 2012/0205645 | A1 | 8/2012 | Fuchs et al. |

FOREIGN PATENT DOCUMENTS

| | | |
|---|---|---|
| EP | 0398698 A2 | 11/1990 |
| EP | 1273595 A1 | 1/2003 |
| EP | 1283222 A1 | 2/2003 |
| EP | 1167455 A1 | 4/2004 |
| EP | 1538167 A1 | 6/2005 |
| EP | 1783145 A1 | 5/2007 |
| EP | 2319874 A1 | 5/2011 |
| WO | 9632426 A1 | 10/1996 |
| WO | 9632427 A1 | 10/1996 |
| WO | 0123441 A1 | 4/2001 |
| WO | 02070569 A1 | 9/2002 |
| WO | 03068828 A1 | 8/2003 |
| WO | 2006010414 A1 | 2/2006 |
| WO | 2006056338 A1 | 6/2006 |
| WO | 2007134851 A1 | 11/2007 |
| WO | 2013124063 A1 | 8/2013 |

OTHER PUBLICATIONS

Armstrong et al. "The Ring-stacking Principle in Organolithium Chemistry: its Development through the Isolation and Crystal Structures of Hexameric Iminolithium Clusters (RR'C=NLi)6(R'=Ph, R = But or Me2N; R 'R'= Me2N or But)" J. Chem. Soc. 1987, 11 pgs.

Bartoli, G. et al. "Convenient procedure for the reduction of β-enamino ketones: synthesis of γ-amino alcohols and tetrahydro-1,3-oxazines", Journal of the Chemical Society, Perkin Transactions 1, 1994, Issue 5, pp. 537-543.

Caron, S. et al. "Preparation and Utility of Trihaloethyl Imidates: Useful Reagents for the Synthesis of Amidines", Journal of Organic Chemistry, 2010, vol. 75, pp. 945-947.

Farmer, J. et al. "Azomethine derivatives. Part XVI. Some diphenylmethyleneaminosilanes and di-t-butylmethyleneaminosilanes", Journal of the Chemical Society, Dalton Transactions, 1972, Issue 14, pp. 1501-1505.

International Search Report for International Application No: PCT/EP2014/067184; International Filing Date: Aug. 11, 2014; Date of Mailing: Oct. 16, 2014; 5 Pages.

Kretschmer, W. et al. "A highly efficient titanium-based olefin polymerisation catalyst with a monoanionic iminoimidazolidide π-donor ancillary ligand", Chemical Communications, 2002, pp. 608-609.

Martinelli, J. et al. "Palladium-Catalyzed Carbonylation Reactions of Aryl Bromides at Atmospheric Pressure: A General System Based on Xantphos", Journal of Organic Chemistry, Sep. 2008, vol. 73, pp. 7102-7107.

Pullukat, T. et al. "Silica-Based Ziegler—Natta Catalysts: A Patent Review", Catalysis Reviews: Science and Engineering, 1999, vol. 41, Issues 3-4, pp. 389-428.

Takabe, K. et al. "Addition of Dialkylamines to Myrcene: N,N-Diethylgeranylamine [2,6-Octadien-1-amine, N,N-diethyl-3,7-dimethyl-,(E)-]", Organice Syntheses, Coll. Vol. 8, p. 188 (1993): vol. 67, p. 44 (1989).

Written Opinion of the International Searching Authority for International Application No. PCT/EP2014/067184; International Filing Date: Aug. 11, 2014; Date of Mailing; Oct. 16, 2014; 6 Pages.

Mironov et al., "Conversions of Compounds with a Si-N=C-X Bond System, Reactions of N-Trialkylsilylimido Esters," pp. 552-554; Translated from Doklady Akademii Nauk SSSR, vol. 199, No. 1. pp. 103-106, Jul. 1971.

Mironov, V. F. et al., Doklady Akademii Nauk. SSSR, 1971,199 (1), 103-106.

S. van der Ven, Polypropylene and other Polyolefins, Elsevier 1990, p. 8-10.

N. Pasquini (ed.) "Polypropylene handbook" 2nd edit on, Carl Hanser Verlag Munich, 2005, Chapter 6.2 11 Pages.

CATALYST SYSTEM FOR POLYMERISATION OF AN OLEFIN

CROSS REFERENCE TO RELATED APPLICATIONS

This application is a 371 of International Application No. PCT/EP2014/067184 filed on Aug. 11, 2014 and claims priority to European Patent application numbers 13199154.9 filed on Dec. 20, 2013 and 13180041.9 filed on Aug. 12, 2013, which are incorporated herein by reference in their entirety.

The present invention relates to a catalyst system comprising a Ziegler-Natta type procatalyst, a co-catalyst and an external electron donor comprising a silicon compound. The invention also relates to a process for obtaining a polyolefin by applying said catalyst system and to a polyolefin obtainable by said process. The invention also relates to the use of said silicon compound as an external electron donor for polymerisation of an olefin.

BACKGROUND

Catalyst systems and their components that are suitable for preparing a polyolefin are generally known. One type of such catalysts are generally referred to as Ziegler-Natta catalysts. The term "Ziegler-Natta" is known in the art and it typically refers to catalyst systems comprising a transition metal-containing solid catalyst compound (also typically referred to as a procatalyst); an organometallic compound (also typically referred to as a co-catalyst) and optionally one or more electron donor compounds (e.g. external electron donors).

The transition metal-containing solid catalyst compound comprises a transition metal halide (e.g. titanium halide, chromium halide, hafnium halide, zirconium halide, vanadium halide) supported on a metal or metalloid compound (e.g. a magnesium compound or a silica compound). An overview of such catalyst types is for example given by T. Pullukat and R. Hoff in Catal. Rev.—Sci. Eng. 41, vol. 3 and 4, 389-438, 1999. The preparation of such a procatalyst is for example disclosed in WO96/32427 A1.

The present invention is related to specific external donors. One of the functions of an external donor compound is to affect the stereoselectivity of the catalyst system in polymerization of olefins having three or more carbon atoms. Therefore it may be also referred to as a selectivity control agent.

The use of silicon compounds as external donors is known in the prior art as being used as external electron donors in Ziegler-Natta catalyst systems for polymerization of olefins. The art presently recognizes a finite set of compounds suitable for use as external donors.

Documents EP1538167 and EP1783145 disclose a Ziegler-Natta catalyst type comprising an organo-silicon compound as external donor that is represented by formula Si(OR$^c$)$_3$(NR$^d$R$^e$), wherein R$^c$ is a hydrocarbon group having 1 to 6 carbon atoms, R$^d$ is a hydrocarbon group having 1 to 12 carbon atoms or hydrogen atom, and R$^e$ is a hydrocarbon group having 1 to 12 carbon atoms used as an external electron donor.

Typical external donors known in the art (for instance as disclosed in documents WO2006/056338A1, EP1838741B1, U.S. Pat. No. 6,395,670B1, EP398698A1, WO96/32426A) are organosilicon compounds having general formula Si(OR$^a$)$_{4-n}$R$^b_n$, wherein n can be from 0 up to 2, and each R$^a$ and R$^b$, independently, represents an alkyl or aryl group, optionally containing one or more hetero atoms for instance O, N, S or P, with, for instance, 1-20 carbon atoms; such as n-propyl trimethoxysilane (nPTMS), n-propyl triethoxysilane (nPEMS), diisobutyl dimethoxysilane (DiBDMS), tert-butyl isopropyl dimethoxysilane (tBiPDMS), cyclohexyl methyldimethoxysilane (CHMDMS), dicyclopentyl dimethoxysilane (DCPDMS), di(iso-propyl) dimethoxysilane (DiPDMS) or di(iso-butyl) dimethoxysilane (diBDMS).

However, by using such external electron donors known in the prior art, high formation of lumps in the powder polymer products within the reactor vessel and in the powder polymer product occurs. Polymer chunks not only hamper production, reducing reaction and production rates but also induce a greater amount of risks, such as injuries and fire while removing polymer chunks using normal maintenance practices. In addition, lumps in the product result in a non-uniform size product and lumps inside the reactor vessel can result in stoppage of the process requiring cleaning of the reactor vessel before the process can be continued. This can be quite costly and time consuming.

There is, therefore, an on-going need in industry for catalysts showing better or varied performance in polymerization of olefins without hampering production of polyolefins.

It is thus an object of the invention to provide an improved catalyst system that allows obtaining of a polyolefin, especially for example a polypropylene-based polymer, with a minimized formation of polymer agglomerates and lumps in the reactor for making the polyolefin.

SUMMARY OF THE INVENTION

This object is achieved with a catalyst system for polymerization of an olefin comprising a Ziegler-Natta type procatalyst, a co-catalyst and an external electron donor, wherein the external electron donor has the structure according to Formula I:

$$Si(L)_n(OR^{11})_{4-n} \quad \text{(Formula I)},$$

wherein,
Si is a silicon atom with valency 4+;
O is an oxygen atom with valency 2− and O is bonded to Si via a silicon-oxygen bond;
n is 1, 2, 3 or 4;
R$^{11}$ is selected from the group consisting of linear, branched and cyclic alkyl having at most 20 carbon atoms and aromatic substituted and unsubstituted hydrocarbyl having 6 to 20 carbon atoms; and
L is a group represented by the following structure

wherein,
L is bonded to the silicon atom via a nitrogen-silicon bond;
L has a single substituent on the nitrogen atom, where this single substituent is an imine carbon atom; and
X and Y are each independently selected from the group consisting of:
a) a hydrogen atom;
b) a group comprising a heteroatom selected from group 13, 14, 15, 16 or 17 of the IUPAC Periodic Table of the Elements, through which X and Y are each independently bonded to the imine carbon atom of Formula II, wherein the heteroatom is substituted with a group consisting of a linear, branched and cyclic alkyl having at most 20 carbon atoms, optionally containing a heteroatom selected from group 13, 14, 15, 16 or 17 of the IUPAC Periodic Table of the Elements; and/or with an aromatic substituted and unsubstituted hydrocarbyl having 6 to 20 carbon atoms, optionally containing a heteroatom selected from group 13, 14, 15, 16 or 17 of the IUPAC Periodic Table of the Elements;

c) a linear, branched and cyclic alkyl having at most 20 carbon atoms, optionally containing a heteroatom selected from group 13, 14, 15, 16 or 17 of the IUPAC Periodic Table of the Elements; and d) an aromatic substituted and unsubstituted hydrocarbyl having 6 to 20 carbon atoms, optionally containing a heteroatom selected from group 13, 14, 15, 16 or 17 of the IUPAC Periodic Table of the Elements.

In an embodiment of the present catalyst system, L is guanidine, amidine or ketimide.

In another embodiment of the present catalyst system, $R^{11}$ is an alkyl having at most 10 carbon atoms.

With the use of the external donors according to the present invention an improved catalyst system is obtained that allows obtaining of a polyolefin, preferably a propylene-based polymer with a minimized tendency to form polymer agglomerates and lumps in the reactor for making the polyolefin. This is assumed to be due to the fact that the polyolefin according to the invention is less/not sticky and thus less prone to form (powder) agglomerates and lumps.

Another advantage of the present invention is that with the use of the external donors according to the present invention an improved catalyst system is obtained having high hydrogen and ethylene response.

A further advantage of the present invention is that with the present catalyst system polypropylene having high isotacticity is obtained.

The external electron donor according to the present invention exhibits high compatibility with Ziegler-Natta type procatalyst and contribute to high catalyst activity, high hydrogen response and high ethylene response when combined with the procatalyst and the co-catalyst, while minimizing the formation of polymer agglomerates or lumps in the reactor for making polyolefins, particularly polypropylene.

In addition, the external donors according to the present invention produce polyolefins with high isotacticity and high melt flow rates when used in Ziegler-Natta catalyst systems.

Furthermore, the catalyst system according to the present invention comprising the specific external donor according to Formula I allows obtaining of propylene-ethylene copolymers, which have a high isotacticity and high melt flow rate, while the catalyst system exhibits a high hydrogen and ethylene response, and in the same time minimizing formation of lumps in the reactor.

Moreover, by using the catalyst system according to the present invention comprising the special external donor of Formula (I), propylene-ethylene random copolymers having a more random distribution of the ethylene comonomer in the polymer chain can be obtained. Also, the rubber content in a heterophasic polypropylene composition may be increased by using the catalyst system according to the invention.

In a second aspect, the present invention relates to a process for preparing the catalyst system according to the invention, comprising contacting a Ziegler-Natta type procatalyst, a co-catalyst and an external electron donor comprising the compound according to Formula I. In an embodiment, said process comprising the steps of:

A) providing a Ziegler-Natta procatalyst obtainable via a process comprising the steps of:

i) contacting a compound $R^4{}_z MgX^4{}_{2-z}$ with an alkoxy- or aryloxy-containing silane compound to give a first intermediate reaction product, being a solid $Mg(OR^1)_x X^1{}_{2-x}$, wherein: $R^4$ is the same as $R^1$ being a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms and preferably has from 1 to 20 carbon atoms; $X^4$ and $X^1$ are each independently selected from the group of consisting of fluoride (F—), chloride (Cl—), bromide (Br—) or iodide (I—), preferably chloride; z is in a range of larger than 0 and smaller than 2, being 0<z<2;

ii) optionally contacting the solid $Mg(OR^1)_x X^1{}_{2-x}$ obtained in step ii) with at least one activating compound selected from the group formed of activating electron donors and metal alkoxide compounds of formula $M^1(OR^2)_{v-w}(OR^3)_w$ or $M^2(OR^2)_{v-w}(R^3)_w$, to obtain a second intermediate product; wherein $M^1$ is a metal selected from the group consisting of Ti, Zr, Hf, Al or Si; $M^2$ is a metal being Si; v is the valency of $M^1$ or $M^2$; $R^2$ and $R^3$ are each a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms, and preferably has from 1 to 20 carbon atoms;

iii) contacting the first or second intermediate reaction product, obtained respectively in step i) or ii), with a halogen-containing Ti-compound and optionally an internal electron donor to obtain said procatalyst;

B) contacting said procatalyst with a co-catalyst and at least one external electron donor being a compound having the structure according to Formula I.

In another embodiment, $Mg(OR^1)_x X^1{}_{2-x}$ is contacted in step ii) with titanium tetraalkoxide and an alcohol as activating compounds.

In another embodiment, the co-catalyst is a hydrocarbyl aluminum compound represented by the formula $R^{21}{}_m AlX^{21}{}_{3-m}$ wherein m=1 or 2, R is an alkyl, and X is a halide or alkoxide.

In another aspect, the present invention relates to a process for preparing a polyolefin by contacting at least one olefin with the catalyst system according to the present invention or obtainable by a process for preparing the catalyst system according to the present invention. In an embodiment of said process for preparing a polyolefin, the at least one olefin is propylene or a mixture of propylene and ethylene.

In another aspect, the present invention relates to a polyolefin obtainable by the process for preparing a polyolefin, wherein the polyolefin has a lump content below 10 wt %, preferably below 4 wt % and more preferably below 3 wt %. This is assumed to be due to the fact that the polyolefin produced according to the invention is less/not sticky and thus less prone to form lumps.

In an embodiment, the polyolefin is a propylene-based polymer.

In another aspect, the present invention relates to a shaped article comprising the polyolefin according to the invention.

In another aspect, the present invention relates to a compound having the structure according to Formula Ia:

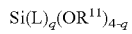

$Si(L)_q(OR^{11})_{4-q}$ (Formula Ia), wherein,
Si is a silicon atom with valency 4+;
O is an oxygen atom with valency 2− and O is bonded to Si via the silicon-oxygen bond;
q is 1, 2 or 3;
$R^{11}$ is a selected from the group consisting of linear, branched and cyclic alkyl having at most 20 carbon atoms and aromatic substituted and unsubstituted hydrocarbyl having 6 to 20 carbon atoms;
L is a group represented by the following structure

wherein,
L is bonded to the silicon atom via the nitrogen-silicon bond;
L has a single substituent on the nitrogen atom, where this single substituent is an imine carbon atom; and
X and Y are each independently selected from the group consisting of
  a) a hydrogen atom;
  b) a group comprising a heteroatom selected from group 13, 14, 15, 16 or 17 of the IUPAC Periodic Table of the Elements, through which X and Y are each independently bonded to the imine carbon atom of Formula II, wherein the heteroatom is substituted with a group consisting of a linear, branched and cyclic alkyl having at most 20 carbon atoms, optionally containing a heteroatom selected from group 13, 14, 15, 16 or 17 of the IUPAC Periodic Table of the Elements; and/or with an aromatic substituted and unsubstituted hydrocarbyl having 6 to 20 carbon atoms, optionally containing a heteroatom selected from group 13, 14, 15, 16 or 17 of the IUPAC Periodic Table of the Elements;
  c) a linear, branched and cyclic alkyl having at most 20 carbon atoms, optionally containing a heteroatom selected from group 13, 14, 15, 16 or 17 of the IUPAC Periodic Table of the Elements; and
  d) an aromatic substituted and unsubstituted hydrocarbyl having 6 to 20 carbon atoms, optionally containing a heteroatom selected from group 13, 14, 15, 16 or 17 of the IUPAC Periodic Table of the Elements In yet another aspect, the present invention relates to the use of the compound having the structure according to Formula I or Ia as an external electron donor in a Ziegler-Natta type catalyst system for polymerization of an olefin.

Definitions

The following definitions are used in the present description and claims to define the stated subject matter. Other terms not cited below are meant to have the generally accepted meaning in the field.

"Ziegler-Natta catalyst" as used in the present description means: a transition metal-containing solid catalyst compound comprises a transition metal halide selected from titanium halide, chromium halide, hafnium halide, zirconium halide, and vanadium halide, supported on a metal or metalloid compound (e.g. a magnesium compound or a silica compound).

"Ziegler-Natta catalytic species" or "catalytic species" as used in the present description means: a transition metal-containing species comprises a transition metal halide selected from titanium halide, chromium halide, hafnium halide, zirconium halide and vanadium halide, "internal donor" or "internal electron donor" or "ID" as used in the present description means: an electron-donating compound containing one or more atoms of oxygen (O) and/or nitrogen (N). This ID is used as a reactant in the preparation of a solid procatalyst. An internal donor is commonly described in prior art for the preparation of a solid-supported Ziegler-Natta catalyst system for olefins polymerization; i.e. by contacting a magnesium-containing support with a halogen-containing Ti compound and an internal donor.

"external donor" or "external electron donor" or "ED" as used in the present description means: an electron-donating compound used as a reactant in the polymerisation of olefins. An ED is a compound added independent of the procatalyst. It is not added during procatalyst formation. It contains at least one functional group that is capable of donating at least one pair of electrons to a metal atom. The ED may influence catalyst properties, non-limiting examples thereof are affecting the stereoselectivity of the catalyst system in polymerization of olefins having 3 or more carbon atoms, hydrogen sensitivity, ethylene sensitivity, randomness of co-monomer incorporation and catalyst productivity.

"activator" as used in the present description means: an electron-donating compound containing one or more atoms of oxygen (O) and/or nitrogen (N) which is used to during the synthesis of the procatalyst prior to or simultaneous with the addition of an internal donor.

"activating compound" as used in the present description means: a compound used to activate the solid support prior to contacting it with the catalytic species.

"modifier" or "Group 13- or transition metal modifier" as used in the present description means: a metal modifier comprising a metal selected from the metals of Group 13 of the IUPAC Periodic Table of elements and transition metals. Where in the description the terms metal modifier or metal-based modifier is used, Group 13- or transition metal modifier is meant.

"procatalyst" and "catalyst component" as used in the present description have the same meaning: a component of a catalyst composition generally comprising a solid support, a transition metal-containing catalytic species and optionally one or more internal donor.

"halide" or "halide ion" or "halogen" or "halogen atom" as used in the present description means: an ion selected from the group of: fluoride (F—), chloride (Cl—), bromide (Br—) or iodide (I—).

"Heteroatom" as used in the present description means: an atom other than carbon or hydrogen. However, as used herein—unless specified otherwise, such as below, —when "one or more hetereoatoms" is used one or more of the following is meant: F, Cl, Br, I, N, O, P, B, S or Si. Thus a heteroatom also includes halides.

"heteroatom selected from group 13, 14, 15, 16 or 17 of the IUPAC Periodic Table of the Elements" as used in the present description means: a hetero atom selected from B, Al, Ga, In, Tl [Group 13], Si, Ge, Sn, Pb [Group 14], N, P, As, Sb, Bi [Group 15], O, S, Se, Te, Po [Group 16], F, Cl, Br, I, At [Group 17]. More preferably, "heteroatom selected from group 13, 14, 15, 16 or 17 of the IUPAC Periodic Table of the Elements" includes N, O, P, B, S, or Si.

"hydrocarbyl" as used in the present description means: is a substituent containing hydrogen and carbon atoms, or linear, branched or cyclic saturated or unsaturated aliphatic radical, such as alkyl, alkenyl, alkadienyl and alkynyl; alicyclic radical, such as cycloalkyl, cycloalkadienyl cycloalkenyl; aromatic radical, such as monocyclic or polycyclic aromatic radical, as well as combinations thereof, such as alkaryl and aralkyl.

"substituted hydrocarbyl" as used in the present description means: is a hydrocarbyl group that is substituted with one or more non-hydrocarbyl substituent groups. A non-limiting example of a non-hydrocarbyl substituent is a heteroatom. Examples are alkoxycarbonyl (viz. carboxylate) groups. When in the present description "hydrocarbyl" is used it can also be "substituted hydrocarbyl", unless stated otherwise.

"alkyl" as used in the present description means: an alkyl group being a functional group or side-chain consisting of carbon and hydrogen atoms having only single bonds. An alkyl group may be straight or branched and may be un-substituted or substituted. It may or may not contain heteroatoms, such as oxygen (O), nitrogen (N), phosphorus (P), silicon (Si) or sulphur (S).

"aryl" as used in the present description means: an aryl group being a functional group or side-chain derived from an aromatic ring. An aryl group and may be un-substituted or substituted with straight or branched hydrocarbyl groups. It may or may not contain heteroatoms, such as oxygen (O), nitrogen (N), phosphorus (P), silicon (Si) or sulphur (S). An aryl group also encloses alkaryl groups wherein one or more hydrogen atoms on the aromatic ring have been replaced by alkyl groups.

"aralkyl" as used in the present description means: an arylalkyl group being an alkyl group wherein one or more hydrogen atoms have been replaced by aryl groups "alkoxide" or "alkoxy" as used in the present description means: a functional group or side-chain obtained from a alkyl alcohol. It consist of an alkyl bonded to a negatively charged oxygen atom.

"aryloxide" or "aryloxy" or "phenoxide" as used in the present description means: a functional group or side-chain obtained from an aryl alcohol. It consist of an aryl bonded to a negatively charged oxygen atom.

"Grignard reagent" or "Grignard compound" as used in the present description means: a compound or a mixture of compounds of formula $R^4_z MgX^4_{2-z}$ ($R^4$, z, and $X^4$ are as defined below) or it may be a complex having more Mg clusters, e.g. $R_4Mg_3Cl_2$.

"polymer" as used in the present description means: a chemical compound comprising repeating structural units, wherein the structural units are monomers.

"olefin" as used in the present description means: an alkene.

"olefin-based polymer" or "polyolefin" as used in the present description means: a polymer of one or more alkenes.

"propylene-based polymer" as used in the present description means: a polymer of propylene and optionally a comonomer.

"polypropylene" as used in the present description means: a polymer of propylene.

"copolymer" as used in the present description means: a polymer prepared from two or more different monomers.

"monomer" as used in the present description means: a chemical compound that can undergo polymerization.

"thermoplastic" as used in the present description means: capable of softening or fusing when heated and of hardening again when cooled.

"Polymer composition" as used in the present description means: a mixture of either two or more polymers or of one or more polymers and one or more additives.

"MWD" or "Molecular weight distribution" as used in the present description means: the same as "PDI" or "polydispersity index". It is the ratio of the weight-average molecular weight (Mw) to the number average molecular weight (Mn), viz. Mw/Mn, and is used as a measure of the broadness of molecular weight distribution of a polymer. Mw and Mn are determined by GPC using a Polymer Laboratories PL-GPC220 combined with a Polymer Laboratories PL BV-400 viscomsimeter, and a refractive index detector, and a Polymer Char IR5 infrared detected; the chromatograms were run at 150° C. using 1,2,4-trichlorobenzene as a solvent; the refractive index detector was used to collect the signal for molecular weights. The values for both methods are the same since they both use calibration against standards.

"XS" or "xylene soluble fraction" or "CXS" or "cold soluble xylene fraction" as used in the present description means: the weight percentage (wt. %) of soluble xylene in the isolated polymer, measured according to ASTM D 5492-10.

"lump content" as used in the present description means: the weight percentage of the total isolated polymer weight which does not pass through a sieve having a pore size of 2.8 mm.

"polymerization conditions" as used in the present description means: temperature and pressure parameters within a polymerization reactor suitable for promoting polymerization between the procatalyst and an olefin to form the desired polymer. These conditions depend on the type of polymerization used.

"production rate" or "yield" as used in the present description means: the amount of kilograms of polymer produced per gram of procatalyst consumed in the polymerization reactor per hour, unless stated otherwise.

"MFR" or "Melt Flow rate" as used in the present description is measured at a temperature of 230° C. with 2.16 kg load and measured according to ISO 1133:2005.

Unless stated otherwise, when it is stated that any R group is "independently selected from" this means that when several of the same R groups are present in a molecule they may have the same meaning of they may not have the same meaning. For example, for the compound $R_2M$, wherein R is independently selected from ethyl or methyl, both R groups may be ethyl, both R groups may be methyl or one R group may be ethyl and the other R group may be methyl.

The present invention is described below in more detail. All embodiments described with respect to one aspect of the present invention are also applicable to the other aspects of the invention, unless otherwise stated.

As stated above, the external donors according to the present invention provide a catalyst having high hydrogen and ethylene response.

A further advantage of the present invention is that with the present catalyst system polypropylene having high isotacticity is obtained.

The present invention is related to Ziegler-Natta type catalyst. A Ziegler-Natta type procatalyst generally comprising a solid support, a transition metal-containing catalytic species and optionally one or more internal donors. The present invention moreover relates to a catalyst system comprising a Ziegler-Natta type procatalyst, a co-catalyst and an external electron donor. The term "Ziegler-Natta" is known in the art.

The transition metal-containing solid catalyst compound comprises a transition metal halide (e.g. titanium halide, chromium halide, hafnium halide, zirconium halide, vanadium halide) supported on a metal or metalloid compound (e.g. a magnesium compound or a silica compound).

Specific examples of several types of Ziegler-Natta catalyst as disclosed below.

Preferably, the present invention is related to a so-called TiNo catalyst. It is a magnesium-based supported titanium halide catalyst optionally comprising one or more internal donors.

EP 1 273 595 of Borealis Technology discloses a process for producing an olefin polymerisation procatalyst in the form of particles having a predetermined size range, said process comprising: preparing a solution a complex of a Gp IIa metal and an electron donor by reacting a compound of said metal with said electron donor or a precursor thereof in an organic liquid reaction medium; reacting said complex, in solution, with at least one compound of a transition metal to produce an emulsion the dispersed phase of which contains more than 50 mol % of the Gp IIa metal in said complex; maintaining the particles of said dispersed phase within the average size range 10 to 200 mu m by agitation in the presence of an emulsion stabilizer and solidifying said particles; and recovering, washing and drying said particles to obtain said procatalyst.

EP 0 019 330 of Dow discloses a Ziegler-Natta type catalyst composition. Said olefin polymerization catalyst composition comprising: a) a reaction product of an organo aluminium compound and an electron donor, and b) a solid component which has been obtained by halogenating a magnesium compound with the formula $MgR^1R^2$ wherein $R^1$ is an alkyl, aryl, alkoxide or aryloxide group and $R^2$ is an alkyl, aryl, alkoxide or aryloxide group or halogen, with a halide of tetravalent titanium in the presence of a halohydrocarbon, and contacting the halogenated product with a tetravalent titanium compound.

The Examples of U.S. Pat. No. 5,093,415 of Dow discloses an improved process to prepare a catalyst. Said process includes a reaction between titanium tetrachloride, diisobutyl phthalate, and magnesium diethoxide to obtain a solid material. This solid material is then slurried titanium tetrachloride in a solvent and phthaloyl chloride is added. The reaction mixture is heated to obtain a solid material which is reslurried in a solvent with titanium tetrachloride. Again this was heated and a solid collected. Once again the solid was reslurried once again in a solution of titanium tetrachloride to obtain a catalyst.

Example 2 of U.S. Pat. No. 6,825,146,2 of Dow discloses another improved process to prepare a catalyst. Said process includes a reaction between titanium tetrachloride in solution with a precursor composition—prepared by reacting magnesium diethoxide, titanium tetraethoxide, and titanium tetrachloride, in a mixture of orthocresol, ethanol and chlorobenzene—and ethylbenzoate as electron donor. The mixture was heated and a solid was recovered. To the solid titanium tetrachloride, a solvent and benzoylchloride were added. The mixture was heated to obtain a solid product. The last step was repeated. The resulting solid procatalyst was worked up to provide a catalyst.

U.S. Pat. No. 4,771,024 discloses the preparation of a catalyst on column 10, line 61 to column 11, line 9. The section "catalyst manufacture on silica" is incorporated into the present application by reference. The process comprises combining dried silica with carbonated magnesium solution (magnesium diethoxide in ethanol was bubbled with $CO_2$). The solvent was evaporated at 85° C. The resulting solid was washed and a 50:50 mixture of titanium tetrachloride and chlorobenzene was added to the solvent together with ethylbenzoate. The mixture was heated to 100° C. and liquid filtered. Again TiCl4 and chlorobenzene were added, followed by heating and filtration. A final addition of TiCl4 and chlorobenzene and benzoylchloride was carried out, followed by heating and filtration. After washing the catalyst was obtained.

WO03/068828 discloses a process for preparing a catalyst component on page 91 "preparation of solid catalyst components" which section is incorporated into the present application by reference. Magnesium chloride, toluene, epoxy chloropropane and tributyl phosphate were added under nitrogen to a reactor, followed by heating. Then phthalic anhydride was added. The solution was cooled to −25° C. and $TiCl_4$ was added dropwise, followed by heating. An internal donor was added (1,3-diphenyl-1,3-propylene glycol dibenzoate, 2-methyl-1,3-diphenyl-1,3-propylene glycol dibenzoate, 1,3-diphenyl-1,3-propylene-glycol diproprionate, or 1,3-diphenyl-2-methyl-1,3-propylene glycol diproprionate) and after stirring a solid was obtained and washed. The solid was treated with $TiCl_4$ in toluene twice, followed by washing to obtain said catalyst component.

U.S. Pat. No. 4,866,022 discloses a catalyst component comprises a product formed by: A. forming a solution of a magnesium-containing species from a magnesium carbonate or a magnesium carboxylate; B. precipitating solid particles from such magnesium-containing solution by treatment with a transition metal halide and an organosilane having a formula: $R_nSiR'_{4-n}$, wherein n=0 to 4 and wherein R is hydrogen or an alkyl, a haloalkyl or aryl radical containing one to about ten carbon atoms or a halosilyl radical or haloalkylsilyl radical containing one to about eight carbon atoms, and R, or a halogen: C. reprecipitating such solid particles from a mixture containing a cyclic ether; and D. treating the reprecipitated particles with a transition metal compound and an electron donor. This process for preparing a catalyst is incorporated into the present application by reference.

The procatalyst may be produced by any method known in the art.

The procatalyst may also be produced as disclosed in WO96/32426A; this document discloses a process for the polymerization of propylene using a catalyst comprising a catalyst component obtained by a process wherein a compound with formula $Mg(OAlk)_xCl_y$ wherein x is larger than 0 and smaller than 2, y equals 2−x and each Alk, independently, represents an alkyl group, is contacted with a titanium tetraalkoxide and/or an alcohol in the presence of an inert dispersant to give an intermediate reaction product and wherein the intermediate reaction product is contacted with titanium tetrachloride in the presence of an internal donor, which is di-n-butyl phthalate.

Preferably, the Ziegler-Natta type procatalyst in the catalyst system according to the present invention is obtained by the process as described in WO 2007/134851 A1. In Example I the process is disclosed in more detail. Example I including all sub-examples (IA-IE) is incorporated into the present description. More details about the different embodiments are disclosed starting on page 3, line 29 to page 14 line 29. These embodiments are incorporated by reference into the present description.

In the following part of the description the different steps and phases of the process for preparing the procatalyst according to the present invention will be discussed.

The process for preparing a procatalyst according to the present invention comprises the following phases:

Phase A): preparing a solid support for the procatalyst;

Phase B): optionally activating said solid support obtained in phase A) using one or more activating compounds to obtain an activated solid support;

Phase C): contacting said solid support obtained in phase A) or said activated solid support in phase B) with a catalytic species wherein phase C) comprises one of the following:
  contacting said solid support obtained in phase A) or said activated solid support in phase B) with a catalytic species to obtain said procatalyst; or
  contacting said solid support obtained in phase A) or said activated solid support in phase B) with a catalytic species and one or more internal donors to obtain said procatalyst; or
  contacting said solid support obtained in phase A) or said activated solid support in phase B) with a catalytic species and one or more internal donors to obtain an intermediate product; or contacting said solid support obtained in phase A) or said activated solid support in phase B) with a catalytic species and an activator to obtain an intermediate product;
  optionally Phase D: modifying said intermediate product obtained in phase C) wherein phase D) comprises on of the following:
    modifying said intermediate product obtained in phase C) with a Group 13- or transition metal modifier in case an internal donor was used during phase C), in order to obtain a procatalyst;
    modifying said intermediate product obtained in phase C) with a Group 13- or transition metal modifier and one or more internal donors in case an activator was used during phase C), in order to obtain a procatalyst.

The procatalyst thus prepared can be used in polymerization of olefins using an external donor and a co-catalyst.

The various steps used to prepare the catalyst according to the present invention (and the prior art) are described in more detail below.

Phase A: Preparing a Solid Support for the Catalyst

In the process of the present invention preferably a magnesium-containing support is used. Said magnesium-containing support is known in the art as a typical component of a Ziegler-Natta procatalyst. This step of preparing a solid support for the catalyst is the same as in the prior art process. The following description explains the process of preparing magnesium-based support. Other supports may be used.

Synthesis of magnesium-containing supports, such as magnesium halides, magnesium alkyls and magnesium aryls, and also magnesium alkoxy and magnesium aryloxy compounds for polyolefin production, particularly of polypropylenes production are described for instance in U.S. Pat. No. 4,978,648, WO96/32427A1, WO01/23441 A1, EP1283 222A1, EP1222 214B1; U.S. Pat. No. 5,077,357; U.S. Pat. No. 5,556,820; U.S. Pat. No. 4,414,132; U.S. Pat. No. 5,106,806 and U.S. Pat. No. 5,077,357 but the present process is not limited to the disclosure in these documents.

Preferably, the process for preparing the solid support for the procatalyst according to the present invention comprises the following steps: step o) which is optional and step i).

Step o) Preparation of the Grignard Reagent (Optional)

A Grignard reagent, $R^4_zMgX^4_{2-z}$ used in step i) may be prepared by contacting metallic magnesium with an organic halide $R^4X^4$, as described in WO 96/32427 A1 and WO01/23441 A1. All forms of metallic magnesium may be used, but preferably use is made of finely divided metallic magnesium, for example magnesium powder. To obtain a fast reaction it is preferable to heat the magnesium under nitrogen prior to use.

$R^4$ is a hydrocarbyl group independently selected from alkyl, alkenyl, aryl, aralkyl, alkylaryl, or alkoxycarbonyl groups, wherein said hydrocarbyl group may be linear, branched or cyclic, and may be substituted or unsubstituted; said hydrocarbyl group preferably having from 1 to 20 carbon atoms or combinations thereof. The $R^4$ group may contain one or more heteroatoms.

$X^4$ is selected from the group of consisting of fluoride (F—), chloride (Cl—), bromide (Br—) or iodide (I—). The value for z is in a range of larger than 0 and smaller than 2: $0<z<2$ Combinations of two or more organic halides $R^4X^4$ can also be used.

The magnesium and the organic halide $R^4X^4$ can be reacted with each other without the use of a separate dispersant; the organic halide $R^4X^4$ is then used in excess.

The organic halide $R^4X^4$ and the magnesium can also be brought into contact with one another and an inert dispersant. Examples of these dispersants are: aliphatic, alicyclic or aromatic dispersants containing from 4 up to 20 carbon atoms.

Preferably, in this step o) of preparing $R^4_zMgX^4_{2-z}$, also an ether is added to the reaction mixture. Examples of ethers are: diethyl ether, diisopropyl ether, dibutyl ether, diisobutyl ether, diisoamyl ether, diallyl ether, tetrahydrofuran and anisole. Dibutyl ether and/or diisoamyl ether are preferably used. Preferably, an excess of chlorobenzene is used as the organic halide $R^4X^4$. Thus, the chlorobenzene serves as dispersant as well as organic halide $R^4X^4$.

The organic halide/ether ratio acts upon the activity of the procatalyst. The chlorobenzene/dibutyl ether volume ratio may for example vary from 75:25 to 35:65, preferably from 70:30 to 50:50.

Small amounts of iodine and/or alkyl halides can be added to cause the reaction between the metallic magnesium and the organic halide $R^4X^4$ to proceed at a higher rate. Examples of alkyl halides are butyl chloride, butyl bromide and 1,2-dibromoethane. When the organic halide $R^4X^4$ is an alkyl halide, iodine and 1,2-dibromoethane are preferably used.

The reaction temperature for step o) of preparing $R^4_zMgX^4_{2-z}$ normally is from 20 to 150° C.; the reaction time is normally from 0.5 to 20 hours. After the reaction for preparing $R^4_zMgX^4_{2-z}$ is completed, the dissolved reaction product may be separated from the solid residual products. The reaction may be mixed. The stirring speed can be determined by a person skilled in the art and should be sufficient to agitate the reactants.

Step i) Reacting a Grignard Compound with a Silane Compound

Step i): contacting a compound $R^4_zMgX^4_{2-z}$—wherein $R_4$, $X^4$, and z are as discussed above—with an alkoxy- or aryloxy-containing silane compound to give a first intermediate reaction product. Said first intermediate reaction product is a solid magnesium-containing support.

In step i) a first intermediate reaction product is thus prepared by contacting the following reactants: * a Grignard reagent—being a compound or a mixture of compounds of formula $R^4_zMgX^4_{2-z}$ and * an alkoxy- or aryloxy-containing silane compound. Examples of these reactants are disclosed for example in WO 96/32427 A1 and WO01/23441 A1.

The compound $R^4_zMgX^4_{2-z}$ used as starting product is also referred to as a Grignard compound. In $R^4_zMgX^4_{2-z}$, $X^4$ is preferably chlorine or bromine, more preferably chlorine.

$R^4$ can be an alkyl, aryl, aralkyl, alkoxide, phenoxide, etc., or mixtures thereof. Suitable examples of group $R^4$ are methyl, ethyl, n-propyl, i-propyl, n-butyl, i-butyl, t-butyl, hexyl, cyclohexyl, octyl, phenyl, tolyl, xylyl, mesityl, benzyl, phenyl, naphthyl, thienyl, indolyl. In a preferred embodiment of the invention, $R^4$ represents an aromatic group, for instance a phenyl group.

In the Grignard compound of formula $R^4_zMgX^4_{2-z}$ z is preferably from about 0.5 to 1.5.

The compound $R^4_zMgX^4_{2-z}$ may be prepared in an optional step (step o) which is discussed above), preceding step i) or may be obtained from a different process.

It is explicitly noted that it is possible that the Grignard compound used in step i) may alternatively have a different structure, for example, may be a complex. Such complexes are already known to the skilled person in the art; a particular example of such complexes is $Phenyl_4Mg_3Cl_2$.

The alkoxy- or aryloxy-containing silane used in step i) is preferably a compound or a mixture of compounds with the general formula $Si(OR^5)_{4-n}R^6_n$, Wherein it should be noted that the $R^5$ group is the same as the $R^1$ group. The $R^1$ group originates from the $R^5$ group during the synthesis of the first intermediate reaction product. $R^5$ is a hydrocarbyl group independently selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms, more preferably from 1 to 12 carbon atoms, even more preferably from 1 to 6 carbon atoms. Preferably, said hydrocarbyl group is an alkyl group, preferably having from 1 to 20 carbon atoms, more preferably from 1 to 12 carbon atoms, even more preferably from 1 to 6 carbon atoms, such as for example methyl, ethyl, n-propyl, isopropyl, n-butyl, sec-butyl, iso-butyl, tert-butyl, pentyl or hexyl; most preferably, selected from ethyl and methyl.

$R^6$ is a hydrocarbyl group independently selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms, more preferably from 1 to 12 carbon atoms, even more preferably from 1 to 6 carbon atoms. Preferably, said hydrocarbyl group is an alkyl group, preferably having from 1 to 20 carbon atoms, more preferably from 1 to 12 carbon atoms, even more preferably from 1 to 6 carbon atoms, such as for example methyl, ethyl, n-propyl, isopropyl, n-butyl, sec-butyl, iso-butyl, tert-butyl, or cyclopentyl.

The value for n is in the range of 0 up to 4, preferably n is from 0 up to and including 1.

Examples of suitable silane-compounds include tetramethoxysilane, tetraethoxysilane, methyltrimethoxysilane, methyltributoxysilane, phenyltriethoxy-silane, diethyldiphenoxysilane, n-propyltriethoxysilane, diisopropyldimethoxysilane, diisobutyldimethoxysilane, n-propyltrimethoxysilane, cyclohexyl-methyldimethoxysilane, dicyclopentyldimethoxy-silane, isobutylisopropyldimethoxyl-silane, phenyl-trimethoxysilane, diphenyl-dimethoxysilane, trifluoropropylmethyl-dimethoxysilane, bis(perhydroisoquinolino)-dimethoxysilane, dicyclohexyldimethoxysilane, dinorbornyl-dimethoxysilane, di(n-propyl) dimethoxysilane, di(iso-propyl)-dimethoxysilane, di(n-butyl)dimethoxysilane and/or di(iso-butyl)dimethoxysilane.

Preferably, tetraethoxy-silane is used as silane-compound in preparing the solid Mg-containing compound during step i) in the process according to the present invention.

Preferably, in step i) the silane-compound and the Grignard compound are introduced simultaneously to a mixing device to result in particles of the first intermediate reaction product having advantageous morphology. This is for example described in WO 01/23441 A1. Here, 'morphology' does not only refer to the shape of the particles of the solid Mg-compound and the catalyst made therefrom, but also to the particle size distribution (also characterized as span), its fines content, powder flowability, and the bulk density of the catalyst particles. Moreover, it is well known that a polyolefin powder produced in polymerization process using a catalyst system based on such procatalyst has a similar morphology as the procatalyst (the so-called "replica effect"; see for instance S. van der Ven, Polypropylene and other Polyolefins, Elsevier 1990, p. 8-10). Accordingly, almost round polymer particles are obtained with a length/diameter ratio (l/D) smaller than 2 and with good powder flowability.

As discussed above, the reactants are preferably introduced simultaneously. With "introduced simultaneously" is meant that the introduction of the Grignard compound and the silane-compound is done in such way that the molar ratio Mg/Si does not substantially vary during the introduction of these compounds to the mixing device, as described in WO 01/23441 A1.

The silane-compound and Grignard compound can be continuously or batch-wise introduced to the mixing device. Preferably, both compounds are introduced continuously to a mixing device.

The mixing device can have various forms; it can be a mixing device in which the silane-compound is premixed with the Grignard compound, the mixing device can also be a stirred reactor, in which the reaction between the compounds takes place. The separate components may be dosed to the mixing device by means of peristaltic pumps.

Preferably, the compounds are premixed before the mixture is introduced to the reactor for step i). In this way, a procatalyst is formed with a morphology that leads to polymer particles with the best morphology (high bulk density, narrow particle size distribution, (virtually) no fines, excellent flowability).

The Si/Mg molar ratio during step i) may range from 0.2 to 20. Preferably, the Si/Mg molar ratio is from 0.4 to 1.0.

The period of premixing of the reactants in above indicated reaction step may vary between wide limits, for instance 0.1 to 300 seconds. Preferably premixing is performed during 1 to 50 seconds.

The temperature during the premixing step of the reactants is not specifically critical, and may for instance range from 0° C. to 80° C.; preferably the temperature is from 10° C. to 50° C.

The reaction between said reactants may, for instance, take place at a temperature from −20° C. to 100° C.; for example at a temperature of from 0° C. to 80° C. The reaction time is for example from 1 to 5 hours.

The mixing speed during the reaction depends on the type of reactor used and the scale of the reactor used. The mixing speed can be determined by a person skilled in the art. As a non-limiting example, mixing may be carried out at a mixing speed of from 250 to 300 rpm. In an embodiment, when a blade stirrer is used the mixing speed is from 220 to 280 rpm and when a propeller stirrer is used the mixing speed is from 270 to 330 rpm. The stirrer speed may be increased during the reaction. For example, during the dosing, the speed of stirring may be increased every hour by 20-30 rpm.

Preferably PhMgCl is the Grignard agent used in step i).

The first intermediate reaction product obtained from the reaction between the silane compound and the Grignard compound is usually purified by decanting or filtration followed by rinsing with an inert solvent, for instance a hydrocarbon solvent with for example 1-20 carbon atoms, like pentane, iso-pentane, hexane or heptane. The solid product can be stored and further used as a suspension in said inert solvent. Alternatively, the product may be dried, preferably partly dried, and preferably under mild conditions; e.g. at ambient temperature and pressure.

The first intermediate reaction product obtained by this step i) may comprise a compound of the formula $Mg(OR^1)_x X^1_{2-x}$, wherein:

$R^1$ is a hydrocarbyl group independently selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms, more preferably from 1 to 12 carbon atoms, even more preferably from 1 to 6 carbon atoms. Preferably, said hydrocarbyl group is an alkyl group, preferably having from 1 to 20 carbon atoms, more preferably from 1 to 12 carbon atoms, even more preferably from 1 to 6 carbon atoms. Most preferably selected from ethyl and methyl.

$X^1$ is selected from the group of consisting of fluoride (F—), chloride (Cl—), bromide (Br—) or iodide (I—). Preferably, $X^1$ is chloride or bromine and more preferably, $X^1$ is chloride.

The value for x is in the range of larger than 0 and smaller than 2: $0<z<2$. The value for x is preferably from 0.5 to 1.5.

Phase B: Activating Said Solid Support for the Catalyst

This step of activating said solid support for the catalyst is an optional step that is not required, but is preferred, in the present invention. If this step of activation is carried out, preferably, the process for activating said solid support comprises the following step ii). This phase may comprise one or more stages.

Step ii) Activation of the Solid Magnesium Compound

Step ii): contacting the solid $Mg(OR^1)_x X^1_{2-x}$ with at least one activating compound selected from the group formed by activating electron donors and metal alkoxide compounds of formula $M^1(OR^2)_{v-w}(OR^3)_w$ or $M^2(OR^2)_{v-w}(R^3)_w$, wherein:

$R^2$ is a hydrocarbyl group independently selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms, more preferably from 1 to 12 carbon atoms, even more preferably from 1 to 6 carbon atoms. Preferably, said hydrocarbyl group is an alkyl group, preferably having from 1 to 20 carbon atoms, more preferably from 1 to 12 carbon atoms, even more preferably from 1 to 6 carbon atoms, such as for example methyl, ethyl, n-propyl, isopropyl, n-butyl, sec-butyl, iso-butyl, tert-butyl, pentyl or hexyl; most preferably selected from ethyl and methyl.

$R^3$ is a hydrocarbyl group independently selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms, more preferably from 1 to 12 carbon atoms, even more preferably from 1 to 6 carbon atoms. Preferably, said hydrocarbyl group is an alkyl group, preferably having from 1 to 20 carbon atoms, more preferably from 1 to 12 carbon atoms, even more preferably from 1 to 6 carbon atoms; most preferably selected from methyl, ethyl, n-propyl, isopropyl, n-butyl, sec-butyl, iso-butyl, tert-butyl, and cyclopentyl.

$M^1$ is a metal selected from the group consisting of Ti, Zr, Hf, Al or Si; v is the valency of $M^1$; $M^2$ is a metal being Si; v is the valency of $M^2$ and w is smaller than v.

The electron donors and the compounds of formula $M(OR^2)_{v-w}(OR^3)_w$ and $M(OR^2)_{v-w}(R^3)_w$ may be also referred herein as activating compounds.

In this step either one or both types of activating compounds (viz. activating electron donor or metal alkoxides) may be used.

The advantage of the use of this activation step prior to contacting the solid support with the halogen-containing titanium compound (process phase C) is that a higher yield of polyolefins is obtained per gram of the procatalyst. Moreover, the ethylene sensitivity of the catalyst system in the copolymerisation of propylene and ethylene is also increased because of this activation step. This activation step is disclosed in detail in WO2007/134851 of the present applicant.

Examples of suitable activating electron donors that may be used in step ii) are known to the skilled person and described herein below, i.e. include carboxylic acids, carboxylic acid anhydrides, carboxylic acid esters, carboxylic acid halides, alcohols, ethers, ketones, amines, amides, nitriles, aldehydes, alkoxides, sulphonamides, thioethers, thioesters and other organic compounds containing one or more hetero atoms, such as nitrogen, oxygen, sulphur and/or phosphorus.

Preferably, an alcohol is used as the activating electron donor in step ii). More preferably, the alcohol is a linear or branched aliphatic or aromatic alcohol having 1-12 carbon atoms. Even more preferably, the alcohol is selected from methanol, ethanol, butanol, isobutanol, hexanol, xylenol and benzyl alcohol. Most preferably, the alcohol is ethanol or methanol, preferably ethanol.

Suitable carboxylic acids as activating electron donor may be aliphatic or (partly) aromatic. Examples include formic acid, acetic acid, propionic acid, butyric acid, isobutanoic acid, acrylic acid, methacrylic acid, maleic acid, fumaric acid, tartaric acid, cyclohexanoic monocarboxylic acid, cis-1,2-cyclohexanoic dicarboxylic acid, phenylcarboxylic acid, toluenecarboxylic acid, naphthalene carboxylic acid, phthalic acid, isophthalic acid, terephthalic acid and/or trimellitic acid.

Anhydrides of the aforementioned carboxylic acids can be mentioned as examples of carboxylic acid anhydrides, such as for example acetic acid anhydride, butyric acid anhydride and methacrylic acid anhydride.

Suitable examples of esters of above-mentioned carboxylic acids are formates, for instance, butyl formate; acetates, for instance ethyl acetate and butyl acetate; acrylates, for instance ethyl acrylate, methyl methacrylate and isobutyl methacrylate; benzoates, for instance methylbenzoate and ethylbenzoate; methyl-p-toluate; ethyl-naphthate and phthalates, for instance monomethyl phthalate, dibutyl phthalate, diisobutyl phthalate, diallyl phthalate and/or diphenyl phthalate.

Examples of suitable carboxylic acid halides as activating electron donors are the halides of the carboxylic acids mentioned above, for instance acetyl chloride, acetyl bromide, propionyl chloride, butanoyl chloride, butanoyl iodide, benzoyl bromide, p-toluyl chloride and/or phthaloyl dichloride.

Suitable alcohols are linear or branched aliphatic alcohols with 1-12 C-atoms, or aromatic alcohols. Examples include methanol, ethanol, butanol, isobutanol, hexanol, xylenol and benzyl alcohol. The alcohols may be used alone or in combination. Preferably, the alcohol is ethanol or hexanol.

Examples of suitable ethers are diethyl ether, dibutyl ether, diisoamyl ether, anisole and ethylphenyl ether, 2,2-diisobutyl-1,3-dimethoxypropane, 2,2-dicyclopentyl-1,3-dimethoxypropane, 2-ethyl-2-butyl-1,3-dimethoxypropane, 2-isopropyl-2-isopentyl-1,3-dimethoxypropane and/or 9,9-bis(methoxymethyl) fluorene. Also, cyclic ethers like tetrahydrofuran (THF), or tri-ethers can be used.

Suitable examples of other organic compounds containing a heteroatom as activating electron donor include 2,2,6,6-tetramethyl piperidine, 2,6-dimethylpiperidine, pyridine, 2-methylpyridine, 4-methylpyridine, imidazole, benzonitrile, aniline, diethylamine, dibutylamine, dimethylacetamide, thiophenol, 2-methyl thiophene, isopropyl mercaptan, diethylthioether, diphenylthioether, tetrahydrofuran, dioxane, dimethylether, diethylether, anisole, acetone, triphenylphosphine, triphenylphosphite, diethylphosphate and/or diphenylphosphate.

Examples of suitable metal alkoxides for use in step ii) are metal alkoxides of formulas: $M^1(OR^2)_{v-w}(OR^3)_w$ and $M^2(OR^2)_{v-w}(R^3)_w$ wherein $M^1$, $M^2$, $R^2$, $R^3$, v, and w are as defined herein. $R^2$ and $R^3$ can also be aromatic hydrocarbon groups, optionally substituted with e.g. alkyl groups and can contain for example from 6 to 20 carbon atoms. The $R^2$ and $R^3$ preferably comprise 1-12 or 1-8 carbon atoms. In preferred embodiments $R^2$ and $R^3$ are ethyl, propyl or butyl; more preferably all groups are ethyl groups.

Preferably, $M^1$ in said activating compound is Ti or Si. Si-containing compounds suitable as activating compounds are the same as listed above for step i).

The value of w is preferably 0, the activating compound being for example a titanium tetraalkoxide containing 4-32 carbon atoms in total from four alkoxy groups. The four alkoxide groups in the compound may be the same or may differ independently. Preferably, at least one of the alkoxy groups in the compound is an ethoxy group. More preferably the compound is a tetraalkoxide, such as titanium tetraethoxide.

In the preferred process to prepare the procatalyst, one activating compound can be used, but also a mixture of two or more compounds may be used.

A combination of a compound of $M^1(OR^2)_{v-w}(OR^3)_w$ or $M^2(OR^2)_{v-w}(R^3)_w$ with an electron donor is preferred as activating compound to obtain a catalyst system that for example shows high activity, and of which the ethylene sensitivity can be affected by selecting the internal donor; which is specifically advantageous in preparing copolymers of for example propylene and ethylene.

Preferably, a Ti-based compound, for example titanium tetraethoxide, is used together with an alcohol, like ethanol or hexanol, or with an ester compound, like ethylacetate, ethylbenzoate or a phthalate ester, or together with an ether, like dibutylether, or with pyridine.

If two or more activating compounds are used in step ii) their order of addition is not critical, but may affect catalyst performance depending on the compounds used. A skilled person may optimize their order of addition based on some experiments. The compounds of step ii) can be added together or sequentially.

Preferably, an electron donor compound is first added to the compound with formula $Mg(OR^1)_xX^1_{2-x}$ where after a compound of formula $M^1(OR^2)_{v-w}(OR^3)_w$ or $M^2(OR^2)_{v-w}(R^3)_w$ as defined herein is added. The activating compounds preferably are added slowly, for instance during a period of 0.1-6, preferably during 0.5-4 hours, most preferably during 1-2.5 hours, each.

The first intermediate reaction product that is obtained in step i) can be contacted—when more than one activating compound is used—in any sequence with the activating compounds. In one embodiment, an activating electron donor is first added to the first intermediate reaction product and then the compound $M^1(OR^2)_{v-w}(OR^3)_w$ or $M^2(OR^2)_{v-w}(R^3)_w$ is added; in this order no agglomeration of solid particles is observed. The compounds in step ii) are preferably added slowly, for instance during a period of 0.1-6, preferably during 0.5-4 hours, most preferably during 1-2.5 hours, each.

The molar ratio of the activating compound to $Mg(OR^1)_xX^1_{2-x}$ may range between wide limits and is, for instance, from 0.02 to 1.0. Preferably the molar ratio is from 0.05 to 0.5, more preferably from 0.06 to 0.4, or even from 0.07 to 0.2.

The temperature in step ii) can be in the range from −20° C. to 70° C., preferably from −10° C. to 50° C., more preferably in the range from −5° C. to 40° C., and most preferably in the range from 0° C. to 30° C.

Preferably, at least one of the reaction components is dosed in time, for instance during 0.1 to 6, preferably during 0.5 to 4 hours, more particularly during 1-2.5 hours.

The reaction time after the activating compounds have been added is preferably from 0 to 3 hours.

The mixing speed during the reaction depends on the type of reactor used and the scale of the reactor used. The mixing speed can be determined by a person skilled in the art and should be sufficient to agitate the reactants.

The inert dispersant used in step ii) is preferably a hydrocarbon solvent. The dispersant may be for example an aliphatic or aromatic hydrocarbon with 1-20 carbon atoms. Preferably, the dispersant is an aliphatic hydrocarbon, more preferably pentane, iso-pentane, hexane or heptane, heptane being most preferred.

Starting from a solid Mg-containing product of controlled morphology obtained in step i), said morphology is not negatively affected during treatment with the activating compound during step ii). The solid second intermediate reaction product obtained in step ii) is considered to be an adduct of the Mg-containing compound and the at least one activating compound as defined in step ii), and is still of controlled morphology.

The obtained second intermediate reaction product after step ii) may be a solid and may be further washed, preferably with the solvent also used as inert dispersant; and then stored and further used as a suspension in said inert solvent. Alternatively, the product may be dried, preferably partly dried, preferably slowly and under mild conditions; e.g. at ambient temperature and pressure.

Phase C: Contacting Said Solid Support with the Catalytic Species and Optionally One or More Internal Donors or an Activator.

Phase C: contacting the solid support with a catalytic species. This step can take different forms, such as i) contacting said solid support with a catalytic species to obtain said procatalyst; ii) contacting said solid support with the catalytic species and one or more internal donors to obtain said procatalyst; iii) contacting said solid support with a catalytic species and one or more internal donors to obtain an intermediate product; iv) contacting said solid support with a catalytic species and an activator donor to obtain an intermediate product.

Phase C may comprise several stages. During each of these consecutive stages the solid support is contacted with said catalytic species. In other words, the addition or reaction of said catalytic species may be repeated one or more times.

For example, during stage I of phase C said solid support (first intermediate) or the activated solid support (second intermediate) is first contacted with said catalytic species and optionally subsequently with one or more internal donors. When a second stage is present, during stage II the intermediate product obtained from stage I will be contacted with additional catalytic species which may be the same or different than the catalytic species added during the first stage and optionally one or more internal donors. In case three stages are present, stage III is preferably a repetition of stage II or may comprise the contacting of the product obtained from phase II with both a catalytic species (which may be the same or different as above) and one or more internal donors. In other words, an internal donor may be added during each of these stages or during two or more of these stages. When an internal donor is added during more than one stage it may be the same or a different internal donor.

An activator according to the present invention—if used—may be added either during stage I or stage II or stage III. An activator may also be added during more than one stage.

Preferably, the process of contacting said solid support with the catalytic species and an internal donor comprises the following step iii).

Step iii) Reacting the Solid Support with a Transition Metal Halide

Step iii) reacting the solid support with a transition metal halide (e.g. titanium, chromium, hafnium, zirconium, vanadium) but preferably titanium halide. In the discussion below only the process for a titanium-base Ziegler-Natta procatalyst is disclosed, however, the application is also applicable to other types of Ziegler-Natta procatalysts.

Step iii): contacting the first or second intermediate reaction product, obtained respectively in step i) or ii), with a halogen-containing Ti-compound and optionally an internal electron donor or activator to obtain a third intermediate product.

Step iii) can be carried out after step i) on the first intermediate product or after step ii) on the second intermediate product.

The molar ratio in step iii) of the transition metal to the magnesium preferably is from 10 to 100, most preferably, from 10 to 50.

Preferably, an internal electron donor is also present during step iii). Also mixtures of internal electron donors can be used. Examples of internal electron donors are disclosed below.

The molar ratio of the internal electron donor relative to the magnesium may vary between wide limits, for instance from 0.02 to 0.75. Preferably, this molar ratio is from 0.05 to 0.4; more preferably from 0.1 to 0.4; and most preferably from 0.1 to 0.3.

During contacting the second intermediate product and the halogen-containing titanium compound, an inert dispersant is preferably used. The dispersant preferably is chosen such that virtually all side products formed are dissolved in the dispersant. Suitable dispersants include for example aliphatic and aromatic hydrocarbons and halogenated aromatic solvents with for instance 4-20 carbon atoms. Examples include toluene, xylene, benzene, heptane, o-chlorotoluene and chlorobenzene.

The reaction temperature during step iii) is preferably from 0° C. to 150° C., more preferably from 50° C. to 150° C., and more preferably from 100° C. to 140° C. Most preferably, the reaction temperature is from 110° C. to 125° C.

The reaction time during step iii) is preferably from 10 minutes to 10 hours. In case several stages are present, each stage can have a reaction time from 10 minutes to 10 hours. The reaction time can be determined by a person skilled in the art based on the reactor and the catalyst composition.

The mixing speed during the reaction depends on the type of reactor used and the scale of the reactor used. The mixing speed can be determined by a person skilled in the art and should be sufficient to agitate the reactants.

The obtained reaction product may be washed, usually with an inert aliphatic or aromatic hydrocarbon or halogenated aromatic compound, to obtain the procatalyst of the invention. If desired the reaction and subsequent purification steps may be repeated one or more times.

A final washing is preferably performed with an aliphatic hydrocarbon to result in a suspended or at least partly dried procatalyst, as described above for the other steps.

Optionally an activator is present during step iii) of Phase C instead of an internal donor, this is explained in more detail below in the section of activators.

The molar ratio of the activator relative to the magnesium may vary between wide limits, for instance from 0.02 to 0.5. Preferably, this molar ratio is from 0.05 to 0.4; more preferably from 0.1 to 0.3; and most preferably from 0.1 to 0.2.

Phase D: Modifying Said Catalyst with a Metal-Based Modifier.

This phase D is optional in the present invention. In a preferred process for modifying the supported catalyst, this phase consists of the following steps:

Step iv) modifying the third intermediate product with a metal-modifier to yield a modified intermediate product;

Step v) contacting said modified intermediate product with a titanium halide and optionally on or more internal donors to obtain the present procatalyst.

The order of addition, viz. the order of first step iv) and subsequently step v) is considered to be very important to the formation of the correct clusters of Group 13- or transition metal and titanium forming the modified and more active catalytic centre.

Each of these steps is disclosed in more detail below.

It should be noted that the steps iii), iv) and v) (viz. phases C and D) are preferably carried out in the same reactor, viz. in the same reaction mixture, directly following each other.

Preferably step iv) is carried out directly after step iii) in the same reactor. Preferably, step v) is carried out directly after step iv) in the same reactor.

The transition metal-containing solid catalyst compound according to the present invention comprises a transition metal halide (e.g. titanium halide, chromium halide, hafnium halide, zirconium halide, vanadium halide) supported on a metal or metalloid compound (e.g. a magnesium compound or a silica compound).

Preferably, a magnesium-based or magnesium-containing support is used in the present invention. Such a support is prepared from magnesium-containing support-precursors, such as magnesium halides, magnesium alkyls and magnesium aryls, and also magnesium alkoxy and magnesium aryloxy compounds.

The support may be activated using activation compounds as described in more detail under Phase B.

The catalyst may further be activated during Phase C as discussed for the process. This activation increases the yield of the resulting procatalyst in olefin polymerisation.

Several activators can be used, such as benzamide, alkylbenzoates, and monoesters. Each of these will be discussed below.

A benzamide activator has a structure according to formula X:

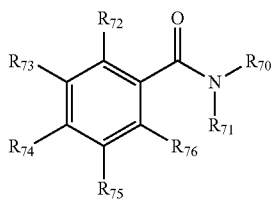

$R^{70}$ and $R^{71}$ are each independently selected from hydrogen or an alkyl. Preferably, said alkyl has from 1 to 6 carbon atoms, more preferably from 1 to 3 carbon atoms. More preferably, $R^{70}$ and $R^{71}$ are each independently selected from hydrogen or methyl.

$R^{72}$, $R^{73}$, $R^{74}$, $R^{75}$, $R^{76}$ are each independently selected from hydrogen, a heteroatom (preferably a halide), or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms.

Suitable non-limiting examples of "benzamides" include benzamide ($R^{70}$ and $R^{71}$ are both hydrogen and each of $R^{72}$, $R^{73}$, $R^{74}$, $R^{75}$, $R^{76}$ are hydrogen) also denoted as BA-2H or methylbenzamide ($R^{70}$ is hydrogen; $R^{71}$ is methyl and each of $R^{72}$, $R^{73}$, $R^{74}$, $R^{75}$, $R^{76}$ are hydrogen) also denoted as BA-HMe or dimethylbenzamide ($R^{70}$ and $R^{71}$ are methyl and each of $R^{72}$, $R^{73}$, $R^{74}$, $R^{75}$, $R^{76}$ are hydrogen) also denoted as BA-2Me. Other examples include monoethylbenzamide, diethylbenzamide, methylethylbenzamide, 2-(trifluormethyl)benzamide, N,N-dimethyl-2-(trifluormethyl)benzamide, 3-(trifluormethyl)benzamide, N,N-dimethyl-3-(trifluormethyl)benzamide, 2,4-dihydroxy-N-(2-hydroxyethyl)benzamide, N-(1H-benzotriazol-1-ylmethyl)benzamide, 1-(4-ethylbenzoyl)piperazine, 1-benzoylpiperidine.

It has surprisingly been found by the present inventors that when the benzamide activator is added during the first stage of the process together with the catalytic species or directly after the addition of the catalytic species (e.g. within 5 minutes) an even higher increase in the yield is observed compared to when the activator is added during stage II or stage III of the process.

It has surprisingly been found by the present inventors that the benzamide activator having two alkyl groups (e.g. dimethylbenzamide or diethylbenzamide, preferably dimethylbenzamide) provides an even higher increase in the yield than either benzamide or monoalkyl benzamide.

Without wishing to be bound by a particular theory the present inventors believe that the fact that the most effective activation is obtained when the benzamide activator is added during stage I has the following reason. It is believed that the benzamide activator will bind the catalytic species and is later on substituted by the internal donor when the internal donor is added.

Alkylbenzoates may be used as activators. The activator may hence be selected from the group alkylbenzoates having an alkylgroup having from 1 to 10, preferably from 1 to 6 carbon atoms. Examples of suitable alkyl benzoates are methylbenzoate, ethylbenzoate according to Formula II, n-propylbenzoate, iso-propylbenzoate, n-butylbenzoate, 2-butylbenzoate, t-butylbenzoate.

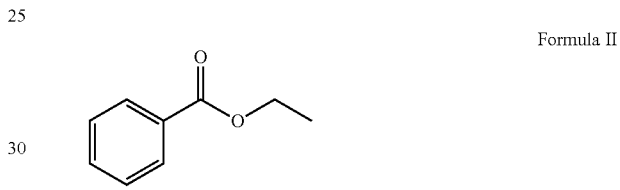

Formula II

More preferably, the activator is ethylbenzoate. In a even more preferred embodiment, ethylbenzoate as activator is added during step iii) and a benzamide internal donor is added during step v), most preferably 4-[benzoyl(methyl)amino]pentan-2-yl benzoate according to Formula XII:

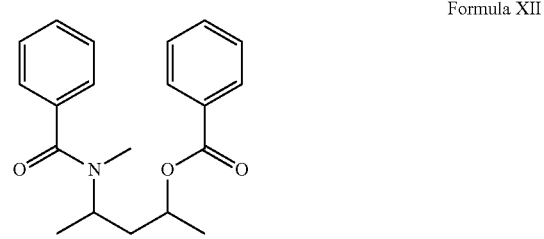 [SMILES: CC(CC(C)N(C)C(=O)c1ccccc1)OC(=O)c1ccccc1]

Formula XII

Mono-esters may be used as activators. The monoester according to the present invention can be any ester of a monocarboxylic acid known in the art. The structures according to Formula V are also mono-esters but are not explained in this section, see the section on Formula V. The monoester can have the formula XXIII

$R^{94}$—CO—O$R^{95}$   Formula XXIII $R^{94}$ and $R^{95}$ are each independently selected from a hydrogen or a hydrocarbyl group selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms. When $R^{94}$ is an aryl, this structure is similar to Formula V. Examples of aromatic mono-esters are discussed with reference to formula V.

Preferably said mono-ester is an aliphatic monoester. Suitable examples of mono-esters include formates, for instance, butyl formate; acetates, for instance ethyl acetate, amyl acetate and butyl acetate; acrylates, for instance ethyl acrylate, methyl methacrylate and isobutyl methacrylate. More preferably, the aliphatic monoester is an acetate. Most preferably, the aliphatic monoester is ethyl acetate.

In an embodiment, the monoester used in step iii) is an ester of an aliphatic monocarboxylic acid having from 1 to 10 carbon atoms. Wherein $R^{94}$ is an aliphatic hydrocarbyl group.

The molar ratio between the monoester in step iii) and Mg may range from 0.05 to 0.5, preferably from 0.1 to 0.4, and most preferably from 0.15 to 0.25.

The monoester is not used as a stereospecificity agent, like usual internal donors are known to be in the prior art. The monoester is used as an activator.

Without to be bound by any theory, the inventors believe that the monoester used in the process according to the present invention participates at the formation of the magnesium halogen (e.g. $MgCl_2$) crystallites during the interaction of Mg-containing support with titanium halogen (e.g. $TiCl_4$). The monoester may form intermediate complexes with Ti and Mg halogen compounds (for instance, $TiCl_4$, $TiCl_3(OR)$, $MgCl_2$, $MgCl(OEt)$, etc.), help to the removal of titanium products from solid particles to mother liquor and affect the activity of final catalyst. Therefore, the monoester according to the present invention can also be referred to as an activator.

As used herein, an "internal electron donor" or an "internal donor" is a compound added during formation of the procatalyst that donates a pair of electrons to one or more metals present in the resultant procatalyst. Not bounded by any particular theory, it is believed that the internal electron donor assists in regulating the formation of active sites thereby enhancing catalyst stereoselectivity.

The internal electron donor can be any compound known in the art to be used as internal electron donor. Suitable examples of internal donors include aromatic acid esters, such as monocarboxylic acid ester or dicarboxylic acid esters (e.f. ortho-dicarboxylic acid esters such as phthalic acid esters), (N-alkyl)amidobenzoates, 1,3-diethers, silyl esters, fluorenes, succinates and/or combinations thereof.

It is preferred to use so-called phthalate free internal donors because of increasingly stricter government regulations about the maximum phthalate content of polymers. This leads to an increased demand in phthalate free catalyst compositions.

An aromatic acid ester can be used as internal donor. As used herein, an "aromatic acid ester" is a monocarboxylic acid ester (also called "benzoic acid ester") as shown in Formula V, a dicarboxylic acid ester (e.g. an o-dicarboxylic acid also called "phtalic acid ester") as shown in Formula VI:

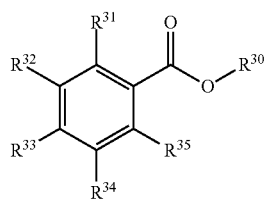

(Formula V)

$R^{30}$ is selected from a hydrocarbyl group independently selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms. Suitable examples of hydrocarbyl groups include alkyl-, cycloalkyl-, alkenyl-, alkadienyl-, cycloalkenyl-, cycloalkadienyl-, aryl-, aralkyl, alkylaryl, and alkynyl-groups.

$R^{31}$, $R^{32}$, $R^{33}$, $R^{34}$, $R^{35}$ are each independently selected from hydrogen, a heteroatom (preferably a halide), or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms.

Suitable non-limiting examples of "benzoic acid esters" include an alkyl p-alkoxybenzoate (such as ethyl p-methoxybenzoate, methyl p-ethoxybenzoate, ethyl p-ethoxybenzoate), an alkyl benzoate (such as ethyl benzoate, methyl benzoate), an alkyl p-halobenzoate (ethyl p-chlorobenzoate, ethyl p-bromobenzoate), and benzoic anhydride. The benzoic acid ester is preferably selected from ethyl benzoate, benzoyl chloride, ethyl p-bromobenzoate, n-propyl benzoate and benzoic anhydride. The benzoic acid ester is more preferably ethyl benzoate.

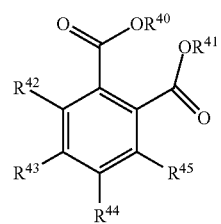

(Formula VI)

$R^{40}$ and $R^{41}$ are each independently a hydrocarbyl group selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms. Suitable examples of hydrocarbyl groups include alkyl-, cycloalkyl-, alkenyl-, alkadienyl-, cycloalkenyl-, cycloalkadienyl-, aryl-, aralkyl, alkylaryl, and alkynyl-groups.

$R^{42}$, $R^{43}$, $R^{44}$, $R^{45}$ are each independently selected from hydrogen, a halide or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms.

Suitable non-limiting examples of phthalic acid esters include dimethyl phthalate, diethyl phthalate, di-n-propyl phthalate, diisopropyl phthalate, di-n-butyl phthalate, diisobutyl phthalate, di-tert-butyl phthalate, diisoamyl phthalate, di-tert-amyl phthalate, dineopentyl phthalate, di-2-ethylhexyl phthalate, di-2-ethyldecyl phthalate, bis(2, 2,2-trifluoroethyl) phthalate, diisobutyl 4-t-butylphthalate, and diisobutyl 4-chlorophthalate. The phthalic acid ester is preferably di-n-butyl phthalate or diisobutyl phthalate.

As used herein a "di-ether" may be a 1,3-di(hydrocarboxy)propane compound, optionally substituted on the 2-position represented by the Formula VII,

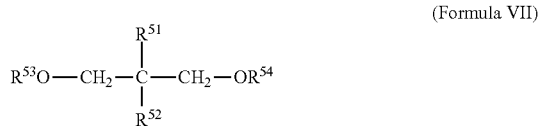

(Formula VII)

$R^{51}$ and $R^{52}$ are each independently selected from a hydrogen or a hydrocarbyl group selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms. Suitable examples of hydrocarbyl groups include alkyl-, cycloalkyl-, alkenyl-, alkadienyl-, cycloalkenyl-, cycloalkadienyl-, aryl-, aralkyl, alkylaryl, and alkynyl-groups.

$R^{53}$ and $R^{54}$ are each independently selected from hydrogen, a halide or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms.

Suitable examples of dialkyl diether compounds include 1,3-dimethoxypropane, 1,3-diethoxypropane, 1,3-dibutoxypropane, 1-methoxy-3-ethoxypropane, 1-methoxy-3-butoxypropane, 1-methoxy-3-cyclohexoxypropane, 2,2-dimethyl-1,3-dimethoxypropane, 2,2-diethyl-1,3-dimethoxypropane, 2,2-di-n-butyl-1,3-dimethoxypropane, 2,2-diiso-butyl-1,3-dimethoxypropane, 2-ethyl-2-n-butyl-1,3-dimethoxypropane, 2-n-propyl-2-cyclopentyl-1,3-dimethoxypropane, 2,2-dimethyl-1,3-diethoxypropane, 2-n-propyl-2-cyclohexyl-1,3-diethoxypropane, 2-(2-ethylhexyl)-1,3-dimethoxypropane, 2-isopropyl-1,3-dimethoxypropane, 2-n-butyl-1,3-dimethoxypropane, 2-sec-butyl-1,3-dimethoxypropane, 2-cyclohexyl-1,3-dimethoxypropane, 2-phenyl-1,3-diethoxypropane, 2-cumyl-1,3-diethoxypropane, 2-(2-phenylethyl)-1,3-dimethoxypropane, 2-(2-cyclohexylethyl)-1,3-dimethoxypropane, 2-(p-chlorophenyl)-1,3-dimethoxypropane, 2-(diphenylmethyl)-1,3-dimethoxypropane, 2-(1-naphthyl)-1,3-dimethoxypropane, 2-(fluorophenyl)-1,3-dimethoxypropane, 2-(1-decahydronaphthyl)-1,3-dimethoxypropane, 2-(p-t-butylphenyl)-1, 3-dimethoxypropane, 2,2-dicyclohexyl-1,3-dimethoxypropane, 2,2-di-npropyl-1,3-dimethoxypropane, 2-methyl-2-n-propyl-1,3-dimethoxypropane, 2-methyl-2-benzyl-1,3-dimethoxypropane, 2-methyl-2-ethyl-1,3-dimethoxypropane, 2-methyl-2-phenyl-1,3-dimethoxypropane, 2-methyl-2-cyclohexyl-1,3-dimethoxypropane, 2,2-bis(pchlorophenyl)-1,3-dimethoxypropane, 2,2-bis(2-cyclohexylethyl)-1,3-dimethoxypropane, 2-methyl-2-iso butyl-1,3-dimethoxypropane, 2-methyl-2-(2-ethylhexyl)-1,3-dimethoxy propane, 2-methyl-2-isopropyl-1,3-dimethoxypropane, 2,2-diphenyl-1,3-dimethoxypropane, 2,2-dibenzyl-1,3-dimethoxypropane, 2,2-bis(cyclohexylmethyl)-1,3-dimethoxypropane, 2,2-diiso butyl-1,3-diethoxypropane, 2,2-diisobuty 1-1,3-di-n-butoxypropane, 2-iso butyl-2-isopropyl-1,3-dimethoxypropane, 2,2-di-sec-butyl-1,3-dimethoxypropane, 2,2-di-t-butyl-1,3-dimethoxypropane, 2,2-dineopentyl-1,3-dimethoxypropane, 2-isopropyl-2-isopentyl-1,3-dimethoxypropane, 2-phenyl-2-benzyl-1,3-dimethoxypropane, 2-cyclohexyl-2-cyclohexylmethyl-1,3-dimethoxypropane, 2-isopropyl-2-(3, 7-dimethyloctyl) 1,3-dimethoxypropane, 2,2-diisopropyl-1,3-dimethoxypropane, 2-isopropyl-2-cyclohexylmethyl-1,3-dimethoxypropane, 2,2-diisopentyl-1,3-dimethoxypropane, 2-isopropyl-2-cyclohexyl-1,3-dimethoxypropane, 2-isopropyl-2-cyclopentyl-1,3-dimethoxypropane, 2,2-dicylopentyl-1,3-dimethoxypropane, 2-n-heptyl-2-n-pentyl-1,3-dimethoxypropane, 9,9-bis(methoxymethyl)fluorene, 1,3-dicyclohexyl-2,2-bis(methoxymethyl)propane, 3,3-bis(methoxymethyl)-2,5-dimethylhexane, or any combination of the foregoing. In an embodiment, the internal electron donor is 1,3-dicyclohexyl-2,2-bis(methoxymethyl)propane, 3,3-bis(methoxymethyl)-2,5-dimethylhexane, 2,2-dicyclopentyl-1,3-dimethoxypropane and combinations thereof.

Examples of preferred ethers are diethyl ether, dibutyl ether, diisoamyl ether, anisole and ethylphenyl ether, 2,3-dimethoxypropane, 2,3-dimethoxypropane, 2-ethyl-2-butyl-1, 3-dimethoxypropane, 2-isopropyl-2-isopentyl-1,3-dimethoxypropane and 9,9-bis (methoxymethyl) fluorene:

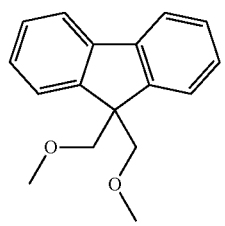 [SMILES: COCC1(COC)c2ccccc2-c2ccccc21]

As used herein a "succinate acid ester" is a 1,2-dicarboxyethane and can be used as internal donor.

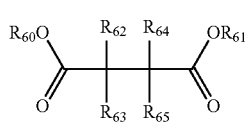

Formula VIII $R^{60}$ and $R^{61}$ are each independently a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms.

$R^{62}$, $R^{63}$, $R^{64}$, and $R^{65}$ are each independently selected from hydrogen or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms.

More preferably, $R^{62}$, $R^{63}$, $R^{64}$, and $R^{65}$ are independently selected from a group consisting of hydrogen, $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group.

Even more preferably, $R^{62}$, $R^{63}$, $R^{64}$, and $R^{65}$ are independently selected from a group consisting of hydrogen, methyl, ethyl, n-propyl, iso-propyl, n-butyl, sec-butyl, iso-butyl, tert-butyl, phenyl trifluoromethyl and halophenyl group. Most preferably, one of $R^{62}$ and $R^{63}$ is selected from methyl, ethyl, n-propyl, iso-propyl, n-butyl, sec-butyl, iso-butyl, tert-butyl, whereas the other is a hydrogen atom; and one of $R^{64}$ and $R^{65}$ is selected from methyl, ethyl, n-propyl, iso-propyl, n-butyl, sec-butyl, iso-butyl, tert-butyl, whereas the other is a hydrogen atom.

Suitable examples of succinate acid ester include diethyl 2,3-di-isopropylsuccinate, diethyl 2,3-di-n-propylsuccinate, diethyl 2,3-di-isobutylsuccinate, diethyl 2,3-di-sec-butylsuccinate, dimethyl 2,3-di-isopropylsuccinate, dimethyl 2,3-di-n-propylsuccinate, dimethyl 2,3-di-isobutylsuccinate, dimethyl 2,3-di-sec-butylsuccinate.

Examples of other organic compounds containing a heteroatom are thiophenol, 2-methylthiophene, isopropyl mercaptan, diethylthioether, diphenylthio-ether, tetrahydrofuran, dioxane, anisole, acetone, triphenylphosphine, triphenylphosphite, diethylphosphate and diphenylphosphate.

The silyl ester as internal donor can be any silyl ester or silyl diol ester known in the art, for instance as disclosed in US 2010/0130709.

When an aminobenzoate (AB) according to Formula XI is used as an internal donor this ensures a better control of stereochemistry and allows preparation of polyolefins having a broader molecular weight distribution.

Aminobenzoates suitable as internal donor according to the present invention are the compounds represented by Formula (XI):

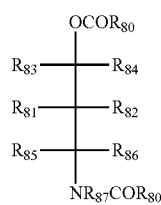

Formula (XI)

Wherein $R^{80}$ is an aromatic group, selected from aryl or alkylaryl groups and may be substituted or unsubstituted. Said aromatic group may contain one or more heteroatoms. Preferably, said aromatic group has from 6 to 20 carbon atoms. It should be noted that the two $R^{80}$ groups may be the same but may also be different.

$R^{80}$ can be the same or different than any of $R^{81}$-$R^{87}$ and is preferably an aromatic substituted and unsubstituted hydrocarbyl having 6 to 10 carbon atoms.

More preferably, $R^{80}$ is selected from the group consisting of $C_6$-$C_{10}$ aryl unsubstituted or substituted with e.g. an acylhalide or an alkoxyde; and $C_7$-$C_{10}$ alkaryl and aralkyl group; for instance, 4-methoxyphenyl, 4-chlorophenyl, 4-methylphenyl.

Particularly preferred, $R^{80}$ is substituted or unsubstituted phenyl, benzyl, naphthyl, ortho-tolyl, para-tolyl oranisol group. Most preferably, $R^{80}$ is phenyl.

$R^{81}$, $R^{82}$, $R^{83}$, $R^{84}$, $R^{85}$, and $R^{86}$ are each independently selected from hydrogen or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms.

More preferably, $R^{81}$, $R^{82}$, $R^{83}$, $R^{84}$, $R^{85}$, and $R^{86}$ are independently selected from a group consisting of hydrogen, $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group.

Even more preferably, $R^{81}$, $R^{82}$, $R^{83}$, $R^{84}$, $R^{85}$, and $R^{86}$ are independently selected from a group consisting of hydrogen, methyl, ethyl, propyl, isopropyl, butyl, tert-butyl, phenyl, trifluoromethyl and halophenyl group.

Most preferably, $R^{81}$, $R^{82}$, $R^{83}$, $R^{84}$, $R^{85}$, and $R^{86}$ are each hydrogen, methyl, ethyl, propyl, tert-butyl, phenyl or trifluoromethyl.

Preferably, $R^{81}$ and $R^{82}$ is each a hydrogen atom.

More preferably, $R^{81}$ and $R^{82}$ is each a hydrogen atom and each of $R^{83}$, $R^{84}$, $R^{85}$, and $R^{86}$ is selected from the group consisting of hydrogen, $C_1$-$C_{10}$ straight and branched alkyls; $C_3$-$C_{10}$ cycloalkyls; $C_6$-$C_{10}$ aryls; and $C_7$-$C_{10}$ alkaryl and aralkyl group.

Preferably, at least one of $R^{83}$ and $R^{84}$ and at least one of $R^{85}$ and $R^{86}$ is a hydrocarbyl group having at least one carbon atom, being selected from the group as defined above.

More preferably, when at least one of $R^{83}$ and $R^{84}$ and one of $R^{85}$ and $R^{86}$ is a hydrocarbyl group having at least one carbon atom then the other one of $R_3$ and $R_4$ and of $R^{85}$ and $R^{86}$ is each a hydrogen atom.

Most preferably, when one of $R^{83}$ and $R^{84}$ and one of $R^{85}$ and $R^{86}$ is a hydrocarbyl group having at least one carbon atom, then the other one of $R^{83}$ and $R^{84}$ and of $R^{85}$ and $R^{86}$ is each a hydrogen atom and $R^{81}$ and $R^{82}$ is each a hydrogen atom.

Preferably, $R^{81}$ and $R^{82}$ is each a hydrogen atom and one of $R^{83}$ and $R^{84}$ and one of $R^{85}$ and $R^{86}$ is selected from the group consisting of $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group.

More preferably $R^{85}$ and $R^{86}$ is selected from the group consisting of $C_1$-$C_{10}$ alkyl, such as methyl, ethyl, propyl, isopropyl, butyl, tert-butyl, phenyl, trifluoromethyl and halophenyl group; and most preferably, one of $R^{83}$ and $R^{84}$, and one of $R^{85}$ and $R^{86}$ is methyl.

$R^{87}$ is a hydrogen or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms, more preferably from 1 to 10 carbon atoms. $R^{87}$ may be the same or different than any of $R^{81}$, $R^{82}$, $R^{83}$, $R^{84}$, $R^{85}$, and $R^{86}$ with the provision that $R^{87}$ is not a hydrogen atom.

More preferably, $R^{87}$ is selected from a group consisting of $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group.

Even more preferably, $R^{87}$ is selected from a group consisting of methyl, ethyl, propyl, isopropyl, butyl, tert-butyl, phenyl, benzyl and substituted benzyl and halophenyl group.

Most preferably, $R^{87}$ is methyl, ethyl, propyl, isopropyl, benzyl or phenyl; and even most preferably, $R^{87}$ is methyl, ethyl or propyl.

Without being limited thereto, particular examples of the compounds of formula (XI) are the structures as depicted in formulas (XII)-(XXII). For instance, the structure in Formula (XII) may correspond to 4-[benzoyl(methyl)amino]pentan-2-yl benzoate; Formula (XIII) to 3-[benzoyl(cyclohexyl)amino]-1-phenylbutyl benzoate; Formula (XIV) to 3-[benzoyl(propan-2-yl)amino]-1-phenylbutyl benzoate; Formula (XV) to 4-[benzoyl(propan-2-yl)amino]pentan-2-yl benzoate; Formula (XVI) to 4-[benzoyl(methyl)amino]-1,1,1-trifluoropentan-2-yl benzoate; Formula (XVII) to 3-(methylamino)-1,3-diphenylpropan-1-oldibenzoate; Formula (XVIII) to 2,2,6,6-tetramethyl-5-(methylamino)heptan-3-ol dibenzoate; Formula (XIX) to 4-[benzoyl (ethyl) amino]pentan-2-yl benzoate; Formula (XX) to 3-(methyl) amino-propan-1-ol dibenzoate; Formula (XXI) to 3-(methyl)amino-2,2-dimethylpropan-1-ol dibenzoate; Formula (XXII) to 4-(methylamino)pentan-2-yl bis (4-methoxy)benzoate).

It has been surprisingly found out that the catalyst composition comprising the compound of formula (XI) as an internal electron donor shows better control of stereochemistry and allows preparation of polyolefins, particularly of polypropylenes having broader molecular weight distribution and higher isotacticity.

Preferably, the catalyst composition according to the invention comprises the compound having formula (XI) as the only internal electron donor in a Ziegler-Natta catalyst composition.

Without being limited thereto, particular examples of the compounds of formula (XI) are the structures as depicted in formulas (XII)-(XXII). For instance, the structure in Formula (XII) may correspond to 4-[benzoyl(methyl)amino]pentan-2-yl benzoate; Formula (XIII) to 3-[benzoyl(cyclohexyl)amino]-1-phenylbutyl benzoate; Formula (XIV) to 3-[benzoyl(propan-2-yl)amino]-1-phenylbutyl benzoate; Formula (XV) to 4-[benzoyl(propan-2-yl)amino]pentan-2-yl benzoate; Formula (XVI) to 4-[benzoyl(methyl)amino]-1,1,1-trifluoropentan-2-yl benzoate; Formula (XVII) to 3-(methylamino)-1,3-diphenylpropan-1-oldibenzoate; Formula (XVIII) to 2,2,6,6-tetramethyl-5-(methylamino)heptan-3-ol dibenzoate; Formula (XIX) to 4-[benzoyl (ethyl) amino]pentan-2-yl benzoate; Formula (XX) to 3-(methyl) amino-propan-1-ol dibenzoate; Formula (XXI) to 3-(methyl)amino-2,2-dimethylpropan-1-ol dibenzoate; Formula (XXII) to 4-(methylamino)pentan-2-yl bis (4-methoxy)benzoate).

The compounds of formula (XII), (XIX), (XXII) and (XVIII) are the most preferred internal electron donors in the catalyst composition according to the present invention as they allow preparation of polyolefins having broader molecular weight distribution and higher isotacticity.

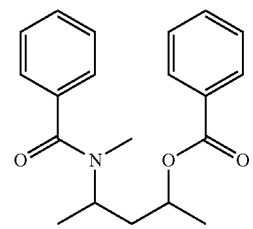

Formula (XII)

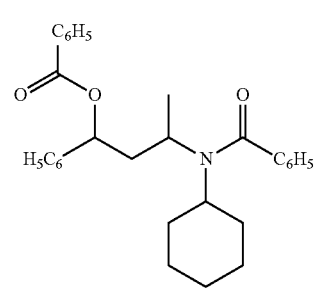

Formula (XIII)

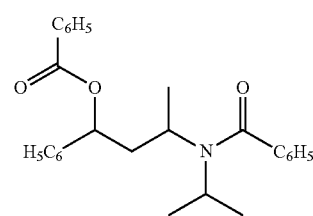

Formula (XIV)

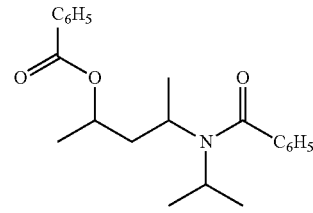

Formula (XV)

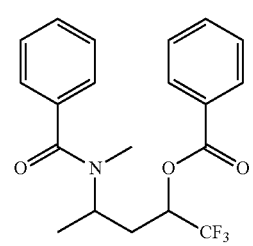

Formula (XVI)

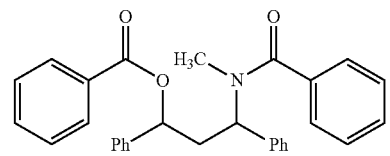

Formula (XVII)

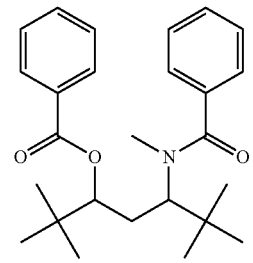

Formula (XVIII)

Formula (XIX)

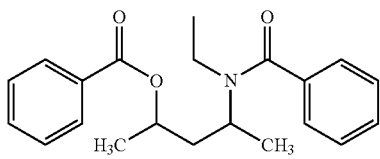

Formula (XX)

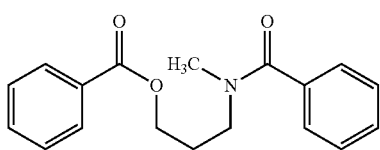

Formula (XXI)

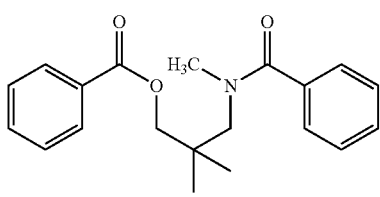

Formula (XXII)

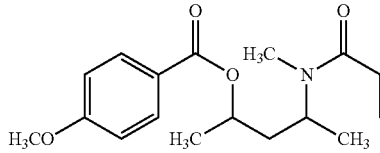

The compound according to formula (XI) can be made by any method known in the art. In this respect, reference is made to J. Chem. Soc. Perkin trans. I 1994, 537-543 and to Org. Synth. 1967, 47, 44. These documents disclose a step a) of contacting a substituted 2,4-diketone with a substituted amine in the presence of a solvent to give a beta-enaminoketone; followed by a step b) of contacting the beta-enaminoketone with a reducing agent in the presence of a solvent to give a gamma-aminoalcohol. The substituted 2,4-diketone and the substituted amine can be applied in step a) in amounts ranging from 0.5 to 2.0 mole, preferably from 1.0 to 1.2 mole. The solvent in steps a) and b) may be added in an amount of 5 to 15 volume, based on the total amount of the diketone, preferably of 3 to 6 volume. The beta-enaminoketone to diketonemole ratio in step b) may be of from 0.5 to 6, preferably from 1 to 3. The reducing agent to beta-enaminoketone mole ratio in step b) may be of from 3 to 8, preferably from 4 to 6; the reducing agent may be selected from the group comprising metallic sodium, NaBH$_4$ in acetic acid, Ni—Al alloy. Preferably, the reducing agent is metallic sodium because it is a cheap reagent.

The gamma-aminoalcohol that can be used for making compound (XI) can be synthesized as described in the literature and also mentioned herein above or this compound can be directly purchased commercially and used as a starting compound in a reaction to obtain the compound represented by formula (XI). Particularly, the gamma-aminoalcohol can be reacted with a substituted or unsubstituted benzoyl chloride in the presence of a base to obtain the compound represented by formula (XI)(referred herein also as step c), regardless that gamma-aminoalcohol was synthesized as described in the literature or commercially purchased. The molar ratio between the substituted or unsubstituted benzoyl chloride and the gamma-aminoalcohol may range from 2 to 4, preferably from 2 to 3. The base may be any basic chemical compound that is able to deprotonate the gamma-aminoalcohol. Said base can have a pK$_a$ of at least 5; or at least 10 or preferably from 5 to 40, wherein pK$_a$ is a constant already known to the skilled person as the negative logarithm of the acid dissociation constant k$_a$. Preferably, the base is pyridine; a trialkyl amine, e.g. triethylamine; or a metal hydroxide e.g. NaOH, KOH. Preferably, the base is pyridine. The molar ratio between the base and the gamma-aminoalcohol may range from 3 to 10, preferably from 4 to 6.

The solvent used in any of steps a), b) and c) can be selected from any organic solvents, such as toluene, dichloromethane, 2-propanol, cyclohexane or mixtures of any organic solvents. Preferably, toluene is used in each of steps a), b) and c). More preferably, a mixture of toluene and 2-propanol is used in step b). The solvent in step c) can be added in an amount of 3 to 15 volume, preferably from 5 to 10 volume based on the gamma-aminoalcohol.

The reaction mixture in any of steps a), b) and c) may be stirred by using any type of conventional agitators for more than about 1 hour, preferably for more than about 3 hours and most preferably for more than about 10 hours, but less than about 24 hours. The reaction temperature in any of steps a) and b) may be the room temperature, i.e. of from about 15 to about 30° C., preferably of from about 20 to about 25° C. The reaction temperature in step c) may range from 0 to 10° C., preferably from 5 to 10° C. The reaction mixture in any of steps a), b) and c) may be refluxed for more than about 10 hours, preferably for more than about 20 hours but less than about 40 hours or until the reaction is complete (reaction completion may be measured by Gas Chromatography, GC). The reaction mixture of steps a) and b) may be then allowed to cool to room temperature, i.e. at a temperature of from about 15 to about 30° C., preferably of from about 20 to about 25° C. The solvent and any excess of components may be removed in any of steps a), b) and c) by any method known in the art, such as evaporation, washing. The obtained product in any of steps b) and c) can be separated from the reaction mixture by any method known in the art, such as by extraction over metal salts, e.g. sodium sulphate.

The molar ratio of the internal donor of formula (XI) relative to the magnesium can be from 0.02 to 0.5. Preferably, this molar ratio is from 0.05 to 0.2.

A benzamide can be used as internal donor. Suitable compounds have a structure according to formula X:

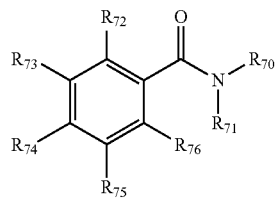

R$^{70}$ and R$^{71}$ are each independently selected from hydrogen or an alkyl. Preferably, said alkyl has from 1 to 6 carbon atoms, more preferably from 1 to 3 carbon atoms. More preferably, R$^{70}$ and R$^{71}$ are each independently selected from hydrogen or methyl.

R$^{72}$, R$^{73}$, R$^{74}$, R$^{75}$, R$^{76}$ are each independently selected from hydrogen, a heteroatom (preferably a halide), or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms.

Suitable non-limiting examples of "benzamides" include benzamide ($R^{70}$ and $R^{71}$ are both hydrogen and each of $R^{72}$, $R^{73}$, $R^{74}$, $R^{75}$, $R^{76}$ are hydrogen) also denoted as BA-2H or methylbenzamide ($R^{70}$ is hydrogen; $R^{71}$ is methyl and each of $R^{72}$, $R^{73}$, $R^{74}$, $R^{75}$, $R^{76}$ are hydrogen) also denoted as BA-HMe or dimethylbenzamide ($R^{70}$ and $R^{71}$ are methyl and each of $R^{72}$, $R^{73}$, $R^{74}$, $R^{75}$, $R^{76}$ are hydrogen) also denoted as BA-2Me. Other examples include monoethylbenzamide, diethylbenzamide, methylethylbenzamide, 2-(trifluormethyl)benzamide, N,N-dimethyl-2-(trifluormethyl)benzamide, 3-(trifluormethyl)benzamide, N,N-dimethyl-3-(trifluormethyl)benzamide, 2,4-dihydroxy-N-(2-hydroxyethyl)benzamide, N-(1H-benzotriazol-1-ylmethyl)benzamide, 1-(4-ethylbenzoyl)piperazine, 1-benzoylpiperidine.

As discussed in WO 2013124063 1,5-diesters according to Formula XXV can be used as internal donors. These 1,5-diesters have two chiral centers on their C2 and C4 carbon atoms. Four isomers exist, being the 2R, 4S meso isomer, the 2S, 4R meso isomers and the 2S, 4S and 2R, 4R isomers. A mixture of all of them is called "rac" diester.

Formula XXV $R^{15}$ is independently a hydrocarbyl group independently selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms.

$R^{16}$ and $R^{17}$ are different with respect to each other. Both $R^{16}$ groups may be the same or different. Both $R^{17}$ groups may be the same or different. The $R^{16}$ and $R^{17}$ groups and independently selected from the group consisting of hydrogen, halogen, and hydrocarbyl group independently selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms.

An example of a compound according to formula XXV is pentanediol dibenzoate.

The compound according to Formula XXV has two stereocenters (at C2 and C4), comprises two so-called stereocenters each giving rise to two different configurations and thus to a total of four stereoisomers. There are two sets of diastereomers (or diastereoisomers), each comprising two enantiomers. Enantiomers differ in both stereocenters and are therefore mirror images of one another.

The $R^{16}$ and the $R^{17}$ groups may be switched in position. In other words, the mirror image of the compound of Formula XXV having the two $R^{17}$ groups on the left hand of the structure. The compound in formula XXV is the (2R, 4S) meso-isomer whereas the mirror image (not shown) is the (2S, 4R) meso-isomer. The compound of Formula XXV is a meso-isomer, i.e. it contains two stereocenters (chiral centers) but it is not chiral.

The following two other isomers are possible: a (2S, 4S)-isomer (not shown), a (2R, 4R)-isomer (not shown). R and S illustrate the chiral centers of the molecules, as known to the skilled person. When a mixture of 2S, 4S and 2R, 4R is present, this is called "rac". These internal donors are disclosed in detail in WO 2013/124063 which shows Fischer projections of all isomers.

In an embodiment, at least one group of $R^{16}$ and $R^{17}$ may be selected from the group consisting of hydrogen, halogen, C1-C10 linear or branched alkyl, C3-C10 cycloalkyl, C6-C10 aryl, and C7-C10 alkaryl or aralkyl group. More preferably, at least one group of $R^{16}$ and $R^{17}$ is selected from the group consisting of hydrogen, methyl, ethyl, propyl, isopropyl, butyl, tert-butyl, phenyl, and halophenyl group.

Preferably, either $R^{16}$ and $R^{17}$ represents hydrogen. More preferably, $R^{16}$ and $R^{17}$ represent a methyl or an ethyl group. Particularly preferred is when either of $R^{16}$ and $R^{17}$ represents hydrogen and the other $R^{16}$ and $R^{17}$ represents a methyl or an ethyl group.

$R^{15}$ is preferably independently selected from benzene-ring containing groups, such as phenyl, phenyl substituted by alkyl, alkoxy or halogen; optionally the carbon atom(s) on the benzene ring being replaced by a hetero-atom of oxygen atom and/or nitrogen atom; alkenyl or phenyl substituted alkenyl, such as vinyl, propenyl, styryl; alkyl, such as methyl, ethyl, propyl, etc.

More preferably, $R^{15}$ represents a phenyl group. Particularly preferred is meso pentane-2,4-diol dibenzoate (mPDDB).

The catalyst system according to the present invention includes a co-catalyst. As used herein, a "co-catalyst" is a term well-known in the art in the field of Ziegler-Natta catalysts and is recognized to be a substance capable of converting the procatalyst to an active polymerization catalyst. Generally, the co-catalyst is an organometallic compound containing a metal from group 1, 2, 12 or 13 of the Periodic System of the Elements (Handbook of Chemistry and Physics, 70th Edition, CRC Press, 1989-1990).

The co-catalyst may include any compounds known in the art to be used as "co-catalysts", such as hydrides, alkyls, or aryls of aluminum, lithium, zinc, tin, cadmium, beryllium, magnesium, and combinations thereof. The co-catalyst may be a hydrocarbyl aluminum co-catalyst represented by the formula $R^{20}{}_3Al$.

$R^{20}$ is independently selected from a hydrogen or a hydrocarbyl, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 20 carbon atoms, more preferably from 1 to 12 carbon atoms, even more preferably from 1 to 6 carbon atoms. On the proviso that at least one $R^{20}$ is a hydrocarbyl group. Optionally, two or three $R^{20}$ groups are joined in a cyclic radical forming a heterocyclic structure.

Non-limiting examples of suitable $R^{20}$ groups are: methyl, ethyl, propyl, isopropyl, butyl, isobutyl, tert-butyl, pentyl, neopentyl, hexyl, 2-methylpentyl, heptyl, octyl, isooctyl, 2-ethylhexyl, 5,5-dimethylhexyl, nonyl, decyl, isodecyl, undecyl, dodecyl, phenyl, phenethyl, methoxyphenyl, benzyl, tolyl, xylyl, naphthyl, methylnapthyl, cyclohexyl, cycloheptyl, and cyclooctyl.

Suitable examples of the hydrocarbyl aluminum compounds as co-catalyst include triisobutylaluminum, trihexylaluminum, di-isobutylaluminum hydride, dihexylaluminum hydride, isobutylaluminum dihydride, hexylaluminum dihydride, diisobutylhexylaluminum, isobutyl dihexylaluminum, trimethylaluminum, triethylaluminum, tripropylaluminum, triisopropylaluminum, tri-n-butylaluminum, trioctylaluminum, tridecylaluminum, tridodecylaluminum, tribenzylaluminum, triphenylaluminum, trinaphthylaluminum, and tritolylaluminum. In an embodiment, the cocatalyst is selected from triethylaluminum, triisobutylaluminum, trihexylaluminum, di-isobutylaluminum hydride and dihexylaluminum hydride. More preferably, trimethylaluminium, triethylaluminium, triisobutylaluminium, and/or trioctylaluminium. Most preferably, triethylaluminium (abbreviated as TEAL).

The co-catalyst can also be a hydrocarbyl aluminum compound represented by the formula $R^{21}_m AlX^{21}_{3-m}$.

$R^{21}$ is an alkyl group. Said alkyl group may be linear, branched or cyclic. Said alkyl group may be substituted or unsubstituted. Preferably, said alkyl group has from 1 to 20 carbon atoms, more preferably from 1 to 12 carbon atoms, even more preferably from 1 to 6 carbon atoms.

Non-limiting examples of suitable $R^{21}$ groups are: methyl, ethyl, propyl, isopropyl, butyl, isobutyl, tert-butyl, pentyl, neopentyl, hexyl, 2-methylpentyl, heptyl, octyl, isooctyl, 2-ethylhexyl, 5,5-dimethylhexyl, nonyl, decyl, isodecyl, undecyl, and dodecyl.

$X^{21}$ is selected from the group of consisting of fluoride (F—), chloride (Cl—), bromide (Br—) or iodide (I—) or an alkoxide (RO⁻). The value for m is preferably 1 or 2.

Non-limiting examples of suitable alkyl aluminium halide compounds for co-catalyst include tetraethyl-dialuminoxane, methylaluminoxane, isobutylaluminoxane, tetraisobutyldialuminoxane, diethyl-aluminumethoxide, diisobutyl-aluminum chloride, methylaluminum dichloride, diethylaluminum chloride, ethylaluminum dichloride and dimethylaluminum chloride.

Non-limiting examples of suitable compounds include tetraethyldialuminoxane, methylaluminoxane, isobutylaluminoxane, tetraisobutyldialuminoxane, diethylaluminum ethoxide, diisobutylaluminum chloride, methylaluminum dichloride, diethylaluminum chloride, ethylaluminum dichloride and dimethylaluminum chloride.

Preferably, the co-catalyst is triethylaluminum. The molar ratio of aluminum to titanium may be from about 5:1 to about 500:1 or from about 10:1 to about 200:1 or from about 15:1 to about 150:1 or from about 20:1 to about 100:1. The molar ratio of aluminum to titanium is preferably about 45:1.

Embodiments of the preferred external donor are discussed below.

Particularly, the L group has a single substituent on the nitrogen atom, this single substituent being a carbon atom which is doubly bonded to the nitrogen atom, which is also defined as the "imine carbon atom".

According to the invention, X and Y can also be each independently selected from a group comprising a heteroatom selected from 13, 14, 15, 16 or 17 groups of the IUPAC Periodic Table of the Elements, through which X and Y are each independently bonded to the imine carbon atom of Formula II, wherein the heteroatom is substituted with a group consisting of a linear, branched and cyclic alkyl having at most 20 carbon atoms, optionally containing a heteroatom selected from group 13, 14, 15, 16 or 17 of the IUPAC Periodic Table of the Elements; and/or with an aromatic substituted and unsubstituted hydrocarbyl having 6 to 20 carbon atoms, optionally containing a heteroatom selected from group 13, 14, 15, 16 or 17 of the IUPAC Periodic Table of the Elements.

Preferably, substituents X and Y are bonded to the imine carbon atom through a group 14, 15 or 16 atom according to the IUPAC Periodic Table of the Elements. More preferably, substituents X and Y are groups bonded to the imine carbon atom through carbon, silicon, nitrogen, phosphorous, oxygen or sulfur. Substituents X and Y are preferably independently selected from a group consisting of a hydrogen atom, alkyl, aryl, and silyl, amide, imide, alkoxy, aryloxy, thioalkoxy, sulphide, phosphide and phosphinimide group of up to 20, for instance 1 to 10 carbon atoms.

More preferably, both substituents X and Y in the L group comprise a nitrogen atom through which X and Y are each bonded to the imine carbon atom. In such case, L is referred herein as a "guanidine" group.

According to the invention, X and Y may be each independently selected from a group consisting of a linear, branched and cyclic alkyl having at most 20 carbon atoms, optionally containing a heteroatom selected from group 13, 14, 15, 16 or 17 of the IUPAC Periodic Table of the Elements; and an aromatic substituted and unsubstituted hydrocarbyl having 6 to 20 carbon atoms, optionally containing a heteroatom selected from group 13, 14, 15, 16 or 17 of the IUPAC Periodic Table of the Elements.

Preferably, L group comprises a substituent X comprising a carbon atom by which X is bonded to the imine carbon atom and a substituent Y comprising a carbon atom by which Y is bonded to the imine carbon atom. In such case, L is referred herein as a "ketimide" group.

More preferably, L group comprises a substituent X comprising a carbon atom, by which X is bonded to the imine carbon atom and Y comprises a nitrogen atom, through which Y is bonded to the imine carbon atom. In such case, L is referred herein as an "amidine" group.

The substituents X and Y may also be linked to each other by a spacer group, which results in X and Y together with the imine carbon atom being part of a ring system. The spacer group may be any hydrocarbon group having 1 to 20 carbon atoms, such as —(CH2)$_n$-, with n being 1 to 20, preferably 1 to 10 carbon atoms and more preferably 1 to 6 carbon atoms. Most preferably, the spacer is an ethylene or propylene group, such as —(CH2)$_n$- with n being 2 or 3.

The present invention also relates to a compound having the structure according to Formula Ia:

$$Si(L)_q(OR^{11})_{4-q} \qquad \text{(Formula Ia)},$$

wherein,
Si is a silicon atom with valency 4+;
O is an oxygen atom with valency 2– and O is bonded to Si via a silicon-oxygen bond;
q is 1, 2 or 3;
$R^{11}$ is a selected from the group consisting of linear, branched and cyclic alkyl having at most 20 carbon atoms and aromatic substituted and unsubstituted hydrocarbyl having 6 to 20 carbon atoms;
L is a group represented by the following structure

wherein,

L is bonded to the silicon atom via a nitrogen-silicon bond;
L has a single substituent on the nitrogen atom, where this single substituent is an imine carbon atom; and
X and Y are each independently selected from the group consisting of:
a) a hydrogen atom;
b) a group comprising a heteroatom selected from group 13, 14, 15, 16 or 17 of the IUPAC Periodic Table of the Elements, through which X and Y are each independently bonded to the imine carbon atom of Formula II, wherein the heteroatom is substituted with a group consisting of a linear, branched and cyclic alkyl having at most 20 carbon atoms, optionally containing a heteroatom selected from group 13, 14, 15, 16 or 17 of the IUPAC Periodic Table of the Elements; and/or with an aromatic substituted and unsubstituted hydrocarbyl having 6 to 20 carbon atoms, optionally containing a heteroatom selected from group 13, 14, 15, 16 or 17 of the IUPAC Periodic Table of the Elements;
c) a linear, branched and cyclic alkyl having at most 20 carbon atoms, optionally containing a heteroatom selected from group 13, 14, 15, 16 or 17 of the IUPAC Periodic Table of the Elements; and
d) an aromatic substituted and unsubstituted hydrocarbyl having 6 to 20 carbon atoms, optionally containing a heteroatom selected from group 13, 14, 15, 16 or 17 of the IUPAC Periodic Table of the Elements.

L and $R^{11}$ of Formula Ia are the same as L and $R^{11}$ as defined herein for Formula I.

The silane compounds according to Formula I and Ia can be synthesized by any methods known in the art, e.g. by reacting a metal salt of group L, such as of a ketimine, amidine or guanidine with $Si(OR^{11})_4$ or $(Z_nSi(OR^{11})_{4-n})$ at different molar ratios, i.e. molar ratio of (metal salts of group L)/$(Si(OR^{11})_4)$ of 1, 2, 3, 4 or excess of metal salt of group L, preferably in a hydrocarbon dispersant or solvent, such as hexane, heptane, pentane, ethers at temperatures from −100° C. to 80° C. The metal salt of group L may be synthesized in situ or isolated by deprotonating a neutral L of Formula II, such as ketimine, amidine or guanidine in a solvent, preferably a hydrocarbon solvent, such as hexane, heptane, pentane, preferably at reaction temperature from −100° C. to 80° C. The deprotonating agent may be chosen from any of the list, which is known by the person skilled in the art. Non-limiting deprotonating agents are lithium diethylamide, n-butyl lithium, t-butyl lithium, methyl magnesium bromide, methyl magnesium chloride, methyl magnesium iodide, ethyl magnesium bromide, sodium hydride, lithium hydride, potassium carbonate and sodium carbonate.

For example, the metal salt of the ketimide can be synthesized by synthetic procedures, which are known from the prior art, e.g. a di-tert-butyl ketimide lithium compound can be synthesized according to a published procedure, D. Armstrong, D. Barr, R. Sanith, *J. Chem. Soc. Dalton Trans.* 1987, 1071. The metal salt of an amidine can be synthesized by synthetic procedures, which are known from the literature, e.g. by reacting an amide anion with a benzonitrile compound (U.S. Pat. No. 7,956,140B2) or the pinner reaction (EP2493906) followed by a deprotonation using a hydrocarbyl lithium or hydrocarbyl magnesium halide compound. The metal salt of a guanidine can be synthesized by synthetic procedures which are known from the literature, e.g. the 1,1,3,3-tetramethyl guanidine anion can be synthesized according to EP10214708 or Journal of the American Chemical Society, 93:7, Apr. 7, 1971, 1502, J. C. S. Dalton (doi:10.1039/DT9720001501).

The metal salt of group L may remain in solution or precipitate from the solvent in which the reaction is performed. In case the metal salt of group L precipitates during the deprotonation reaction, the remaining solid metal salt of group L can be isolated by filtration and purified by multiple washings with additional solvent. In case the metal salt of group L remains in solution, the solution can be used further as such.

Compounds of the invention of Formula I or Ia may also be synthesized by reacting an alkoxy silane halide represented by Formula XXIVa with a metal salt of group L, such as a ketimine, amidine or guanidine preferably in a hydrocarbon dispersant or solvent, such as hexane, heptane, pentane, ethers at temperatures from −100° C. to 80° C. The molar ratios of (metal salt of group L)/$(Z_nSi(OR^{11})_{4-n})$ in this reaction preferably equal n.

Alternatively, compounds of the invention of Formula I or Ia may also be synthesized by reacting a neutral L group, such as a ketimine, amidine or guanidine with an alkoxy silane halide of Formula XXIVa in the presence or in the absence of a base. Non-limiting examples of such bases used are triethyl amine, diethyl amine, DBU and tetraazacyclononane (Mironov, V. F. et al., *Doklady Akademii Nauk. SSSR*, 1971, 199(1), 103-106).

The molar ratio that can be applied in the reaction of the neutral group L equals that of n in Formula XXIVa and the base can be use equimolar to that or, preferably, in excess. The reaction is preferably performed in a hydrocarbon dispersant or solvent, such as alkanes, aromatic solvents or ethereal solvents at temperatures from 25° C. to 150° C. Non-limiting examples of solvents used are hexane, heptane, toluene, p-xylene, diethylether and tetrahydrofuran.

Formula XXIVa

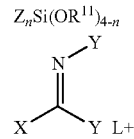

In the alkoxy silane halide represented by Formula XXIVa, Z is halogen group, and more preferably a chlorine group; n=1, 2 or 3; $R^{11}$ is a hydrocarbon group with 1-4 carbon atoms, for example, methyl, ethyl or propyl groups, such as n-propyl, i-propyl, and butyl groups, such as n-butyl, i-butyl, s-butyl and t-butyl groups. The ethyl and methyl groups are especially preferred.

In the protonated L group represented by $L^+$, X and Y are defined the same as for the L group.

Neutral compounds L can be synthesized through methods known in the art, e.g. Caron, Stephane et al., *Journal of Organic Chemistry*, 2010, 75(3), 945-947; Buchwald, S. L. et al., *J. Org. Chem.* 2008, 73, 7102; Zuideveld, M. A. et al. U.S. Pat. No. 7,956,140B2; Kretschmer, W. P. et al., *Chem. Commun.*, 2002, 608 and WO02/070569; Zuideveld, M. A. et al. EP2319874; J. McMeeking et al. U.S. Pat. No. 6,114,481.

In some cases, the compound L can be obtained as its hydrogen halide salt. Specific examples of halogen halides are hydrogen chloride, hydrogen bromide and hydrogen iodide. The neutral compound L-H can be obtained by reacting the hydrogen halide salt of L with a base.

In order to show the structural variety possible for L groups, non-exhaustive examples of L are represented by the following structures:

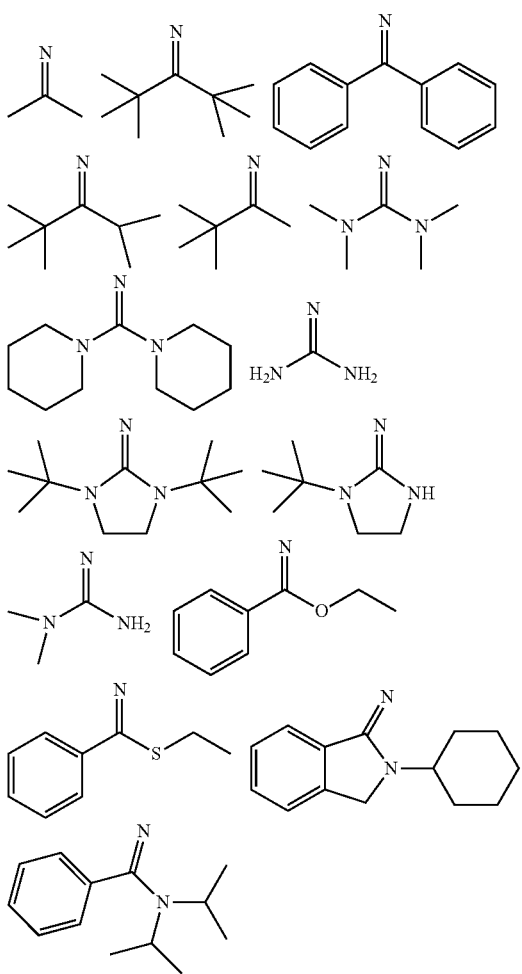

The external electron donor according to the present invention consists of only the compound of Formula I or Ia or the external electron donor comprises the compound of Formula I or Ia and an additional compound.

The additional compound(s) in the external donor according to the invention may be one or more alkoxysilanes. The alkoxysilane compound can have any of the structures disclosed herein. The alkoxysilane is described by Formula IX

$$SiR_r(OR')_{4-r} \qquad \text{(Formula IX)}$$

where R independently is hydrogen or a hydrocarbyl or an amino group optionally substituted with one or more substituents containing one or more Group 14, 15, 16, or 17 heteroatoms of the IUPAC Periodic Table of the Elements, said R containing up to 20 atoms, apart from hydrogen and halogen; R' is a C1-20 alkyl group; and r is 0, 1, 2 or 3. In an embodiment, R is C6-12 aryl, alkyl or aralkyl, C3-12 cycloalkyl, C3-12 branched alkyl, or C3-12 cyclic or acyclic amino group, R' is C1-4 alkyl, and r is 1 or 2. Suitable examples of such silane compositions include dicyclopentyldimethoxysilane, di-tert-butyldimethoxysilane, ethylcyclohexyldimethoxysilane, methylcyclohexyldiethoxysilane, diphenyldimethoxysilane, diiso butyl dimethoxysilane, diisopropyl dimethoxysilane, diisobutyldiethoxysilane, ethylcyclohexyldimethoxysilane, di-n-propyldimethoxysilane, di-n-butyldimethoxysilane, cyclopentyltrimethoxysilane, isopropyltrimethoxysilane, n-propyltrimethoxysilane, n-propyltriethoxysilane, ethyltriethoxysilane, tetramethoxysilane, tetraethoxysilane, diethylaminotriethoxysilane, cyclopentylpyrrolidinodimethoxysilane, bis(pyrrolidino) dimethoxysilane, bis(perhydroisoquinolino)dimethoxysilane, and dimethyldimethoxysilane. In an embodiment, the alkoxysilane is dicyclopentyldimethoxysilane, thylcyclohexyldimethoxysilane, n-propyltrimethoxysilane and any combination thereof. Preferably, the additional external donor is dicyclopentyldimethoxysilane.

The external donor of the present invention may include from about 0.1 mol % to about 99.9% mol % of the silane represented by Formula I and from about 99.9 mol % to about 0.1 mol % of the additional alkoxysilane.

The Si/Ti molar ratio in the catalyst system can range from 0.1 to 40, preferably from 0.1 to 20, even more preferably from 1 to 20 and most preferably from 2 to 10.

The catalyst system according to the present invention comprising the special silicon-based external electron donor as defined herein exhibits at least one of the following properties: improved activity, improved hydrogen response, improved ethylene response and reduced lump formation during polymerization. The catalyst system according to the present invention comprising the special external electron donor as defined herein allows producing olefin-based polymers with high isotacticity, high melt flow rate and high ethylene content in case the polyolefin is a propylene-ethylene copolymer.

The invention also relates to a process to make the catalyst system by contacting a Ziegler-Natta type procatalyst, a co-catalyst and an external electron donor. The procatalyst, the co-catalyst and the external donor can be contacted in any way known to the skilled person in the art; and as also described herein, more specifically as in the Examples.

The invention further relates to a process for making a polyolefin by contacting an olefin with the catalyst system according to the present invention. The procatalyst, the co-catalyst, the external donor and the olefin can be contacted in any way known to the skilled person in the art; and as also described herein.

For instance, the external donor in the catalyst system according to the present invention can be complexed with the co-catalyst and mixed with the procatalyst (pre-mix) prior to contact between the catalyst composition and the olefin. The external donor can also be added independently to the polymerization reactor. The procatalyst, the co-catalyst, and the external donor can be mixed or otherwise combined prior to addition to the polymerization reactor.

Contacting the olefin with the catalyst system according to the present invention can be done under standard polymerization conditions, known to the skilled person in the art. See for example Pasquini, N. (ed.) "Polypropylene handbook" $2^{nd}$ edition, Carl Hanser Verlag Munich, 2005. Chapter 6.2 and references cited therein.

The polymerization process may be a gas phase, a slurry or a bulk polymerization process, operating in one or more than one reactor. One or more olefin monomers can be introduced in a polymerization reactor to react with the catalyst composition and to form an olefin-based polymer (or a fluidized bed of polymer particles).

In the case of polymerization in a slurry (liquid phase), a dispersing agent is present. Suitable dispersing agents include for example propane, n-butane, isobutane, n-pentane, isopentane, hexane (e.g. iso- or n-), heptane (e.g. iso- or n-), octane, cyclohexane, benzene, toluene, xylene, liquid propylene and/or mixtures thereof. The polymerization such as for example the polymerization temperature and time, monomer pressure, avoidance of contamination of catalyst, choice of polymerization medium in slurry processes, the use of further ingredients (like hydrogen) to control polymer molar mass, and other conditions are well known to persons of skill in the art. The polymerization temperature may vary within wide limits and is, for example for propylene polymerization, from 0° C. to 120° C., preferably from 40° C. to 100° C. The pressure during (propylene) (co)polymerization is for instance from 0.1 to 6 MPa, preferably from 1 to 4 MPa.

Several types of polyolefins are prepared such as homopolyolefins, random copolymers and heterophasic polyolefin. For heterophasic polypropylene, the following is observed.

Heterophasic propylene copolymers are generally prepared in one or more reactors, by polymerization of propylene and optionally one or more other olefins, for example ethylene, in the presence of a catalyst and subsequent polymerization of a propylene-α-olefin mixture. The resulting polymeric materials can show multiple phases (depending on monomer ratio), but the specific morphology usually depends on the preparation method and monomer ratio. The heterophasic propylene copolymers employed in the process according to present invention can be produced using any conventional technique known to the skilled person, for example multistage process polymerization, such as bulk polymerization, gas phase polymerization, slurry polymerization, solution polymerization or any combinations thereof. Any conventional catalyst systems, for example, Ziegler-Natta or metallocene may be used. Such techniques and catalysts are described, for example, in WO06/010414; Polypropylene and other Polyolefins, by Ser van der Ven, Studies in Polymer Science 7, Elsevier 1990; WO06/010414, U.S. Pat. No. 4,399,054 and U.S. Pat. No. 4,472,524.

The molar mass of the polyolefin obtained during the polymerization can be controlled by adding hydrogen or any other agent known to be suitable for the purpose during the polymerization. The polymerization can be carried out in a continuous mode or batch-wise. Slurry-, bulk-, and gas-phase polymerization processes, multistage processes of each of these types of polymerization processes, or combinations of the different types of polymerization processes in a multistage process are contemplated herein. Preferably, the polymerization process is a single stage gas phase process or a multistage, for instance a two-stage gas phase process, e.g. wherein in each stage a gas-phase process is used or including a separate (small) prepolymerization reactor.

Examples of gas-phase polymerization processes include both stirred bed reactors and fluidized bed reactor systems; such processes are well known in the art. Typical gas phase olefin polymerization reactor systems typically comprise a reactor vessel to which an olefin monomer(s) and a catalyst system can be added and which contain an agitated bed of growing polymer particles. Preferably the polymerization process is a single stage gas phase process or a multistage, for instance a 2-stage, gas phase process wherein in each stage a gas-phase process is used.

As used herein, "gas phase polymerization" is the way of an ascending fluidizing medium, the fluidizing medium containing one or more monomers, in the presence of a catalyst through a fluidized bed of polymer particles maintained in a fluidized state by the fluidizing medium optionally assisted by mechanical agitation. Examples of gas phase polymerization are fluid bed, horizontal stirred bed and vertical stirred bed.

"fluid-bed," "fluidized," or "fluidizing" is a gas-solid contacting process in which a bed of finely divided polymer particles is elevated and agitated by a rising stream of gas optionally assisted by mechanical stirring. In a "stirred bed" upwards gas velocity is lower than the fluidization threshold.

A typical gas-phase polymerization reactor (or gas phase reactor) include a vessel (i.e., the reactor), the fluidized bed, a product discharge system and may include a mechanical stirrer, a distribution plate, inlet and outlet piping, a compressor, a cycle gas cooler or heat exchanger. The vessel may include a reaction zone and may include a velocity reduction zone, which is located above the reaction zone (viz. bed). The fluidizing medium may include propylene gas and at least one other gas such as an olefin and/or a carrier gas such as hydrogen or nitrogen. The contacting can occur by way of feeding the catalyst composition into the polymerization reactor and introducing the olefin into the polymerization reactor. In an embodiment, the process includes contacting the olefin with a co-catalyst. The co-catalyst can be mixed with the procatalyst (pre-mix) prior to the introduction of the procatalyst into the polymerization reactor. The co-catalyst may be also added to the polymerization reactor independently of the procatalyst. The independent introduction of the co-catalyst into the polymerization reactor can occur (substantially) simultaneously with the procatalyst feed. An external donor may also be present during the polymerization process.

The olefin according to the invention may be selected from mono- and di-olefins containing from 2 to 40 carbon atoms. Suitable olefin monomers include alpha-olefins, such as ethylene, propylene, alpha-olefins having from 4 to 20 carbon atoms (viz. C4-20), such as 1-butene, 1-pentene, 1-hexene, 4-methyl-1-pentene, 1-heptene, 1-octene, 1-decene, 1-dodecene and the like; C4-C20 diolefins, such as 1,3-butadiene, 1,3-pentadiene, norbornadiene, 5-vinyl-2-norbornene (VNB), 1,4-hexadiene, 5-ethylidene-2-norbornene (ENB) and dicyclopentadiene; vinyl aromatic compounds having from 8 to 40 carbon atoms (viz. C8-C40) including styrene, o-, m- and p-methylstyrene, divinylbenzene, vinylbiphenyl, vinylnapthalene; and halogen-substituted C8-C40 vinyl aromatic compounds such as chlorostyrene and fluorostyrene.

Preferably, the olefin is propylene or a mixture of propylene and ethylene, to result in a propylene-based polymer, such as propylene homopolymer or propylene-olefin copolymer. The olefin may an alpha-olefin having up to 10 carbon atoms, such as ethylene, butane, hexane, heptane, octene. A propylene copolymer is herein meant to include both so-called random copolymers which typically have relatively low comonomer content, e.g. up to 10 mol %, as well as so-called impact PP copolymers or heterophasic PP copolymers comprising higher comonomer contents, e.g. from 5 to 80 mol %, more typically from 10 to 60 mol %. The impact PP copolymers are actually blends of different propylene polymers; such copolymers can be made in one or two reactors and can be blends of a first component of low comonomer content and high crystallinity, and a second component of high comonomer content having low crystallinity or even rubbery properties. Such random and impact copolymers are well-known to the skilled in the art. A propylene-ethylene random copolymer may be produced in one reactor. Impact PP copolymers may be produced in two reactors: polypropylene homopolymer may be produced in a first reactor; the content of the first reactor is subsequently transferred to a second reactor into which ethylene (and optionally propylene) is introduced. This results in production of a propylene-ethylene copolymer (i.e. an impact copolymer) in the second reactor.

The present invention also relates to a polyolefin, preferably a polypropylene obtained or obtainable by a process, comprising contacting an olefin, preferably propylene or a mixture of propylene and ethylene with the procatalyst according to the present invention. The terms polypropylene and propylene-based polymer are used herein interchangeable. The polypropylene may be a propylene homopolymer or a mixture of propylene and ethylene, such as a propylene-based copolymer, e.g. heterophasic propylene-olefin copolymer; random propylene-olefin copolymer, preferably the olefin in the propylene-based copolymers being a C2, or C4-C6 olefin, such as ethylene, butylene, pentene or hexene. Such propylene-based (co)polymers are known to the skilled person in the art; they are also described herein above.

The present invention also relates to a polyolefin, preferably a propylene-based polymer obtained or obtainable by a process as described herein above, comprising contacting propylene or a mixture of propylene and ethylene with a catalyst system according to the present invention.

In one embodiment according to the present invention a (random) copolymer of propylene and ethylene monomers is obtained. For such a polymer, properties such as Xs and reduced haze increase after time may be important.

The content of the comonomer used in addition to propylene (e.g. ethylene or C4-C6-olefin) may vary from 0 to 8 wt. % based on the total weight of the polymer, preferably from 1 to 4 wt. %.

C2 content is expressed as weight percentage (wt. %) of ethylene incorporated into the total polymer weight obtained and measured with FT-IR. The FT-IR method was calibrated using NMR data.

Several polymer properties are discussed here.

Xylene soluble fraction (XS) is preferably from about 0.5 wt % to about 10 wt %, or from about 1 wt % to about 8 wt %, or from 2 to 6 wt %, or from about 1 wt % to about 5 wt %. Preferably, the xylene amount (XS) is lower than 6 wt %, preferably lower than 5 wt %, more preferably lower than 4 wt % or even lower than 3 wt % and most preferably lower than 2.7 wt %.

The lump content is preferably below 10 wt %, preferably below 4 wt % and more preferably below 3 wt %.

The production rate is preferably from about 1 kg/g/hr to about 100 kg/g/hr, or from about 10 kg/g/hr to about 40 kg/g/hr.

MFR is preferably from about 0.01 g/10 min to about 2000 g/10 min, or from about 0.01 g/10 min to about 1000 g/10 min; or from about 0.1 g/10 min to about 500 g/10 min, or from about 0.5 g/10 min to about 150 g/10 min, or from about 1 g/10 min to about 100 g/10 min.

The olefin polymer obtained in the present invention is considered to be a thermoplastic polymer. The thermoplastic polymer composition according to the invention may also contain one or more of usual additives, like those mentioned above, including stabilisers, e.g. heat stabilisers, anti-oxidants, UV stabilizers; colorants, like pigments and dyes; clarifiers; surface tension modifiers; lubricants; flame-retardants; mould-release agents; flow improving agents; plasticizers; anti-static agents; impact modifiers; blowing agents; fillers and reinforcing agents; and/or components that enhance interfacial bonding between polymer and filler, such as a maleated polypropylene, in case the thermoplastic polymer is a polypropylene composition. The skilled person can readily select any suitable combination of additives and additive amounts without undue experimentation.

The amount of additives depends on their type and function; typically is of from 0 to about 30 wt %; preferably of from 0 to about 20 wt. %; more preferably of from 0 to about 10 wt % and most preferably of from 0 to about 5 wt. % based on the total composition. The sum of all components added in a process to form the polyolefins, preferably the propylene-base polymers or compositions thereof should add up to 100 wt. %.

The thermoplastic polymer composition of the invention may be obtained by mixing one or more of the thermoplastic polymers with one or more additives by using any suitable means. Preferably, the thermoplastic polymer composition of the invention is made in a form that allows easy processing into a shaped article in a subsequent step, like in pellet or granular form. The composition can be a mixture of different particles or pellets; like a blend of a thermoplastic polymer and a master batch of nucleating agent composition, or a blend of pellets of a thermoplastic polymer comprising one of the two nucleating agents and a particulate comprising the other nucleating agent, possibly pellets of a thermoplastic polymer comprising said other nucleating agent. Preferably, the thermoplastic polymer composition of the invention is in pellet or granular form as obtained by mixing all components in an apparatus like an extruder; the advantage being a composition with homogeneous and well-defined concentrations of the nucleating agents (and other components).

The invention also relates to the use of the polyolefins, preferably the propylene-based polymers (also called polypropylenes) according to the invention in injection moulding, blow moulding, extrusion moulding, compression moulding, casting, thin-walled injection moulding, etc. for example in food contact applications.

Furthermore, the invention relates to a shaped article comprising the polyolefin, preferably the propylene-based polymer according to the present invention.

The polyolefin, preferably the propylene-based polymer according to the present invention may be transformed into shaped (semi)-finished articles using a variety of processing techniques. Examples of suitable processing techniques include injection moulding, injection compression moulding, thin wall injection moulding, extrusion, and extrusion compression moulding. Injection moulding is widely used to produce articles such as for example caps and closures, batteries, pails, containers, automotive exterior parts like bumpers, automotive interior parts like instrument panels, or automotive parts under the bonnet. Extrusion is for example widely used to produce articles, such as rods, sheets, films and pipes. Thin wall injection moulding may for example be used to make thin wall packaging applications both for food and non-food segments. This includes pails and containers and yellow fats/margarine tubs and dairy cups.

It is noted that the invention relates to all possible combinations of features recited in the claims. Features described in the description may further be combined.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will be further elucidated with the following examples without being limited hereto.

EXAMPLES

Synthesis of Si(L)$_n$(OR$^1$)$_{4-n}$ Compounds 1,1,3,3-Tetramethylguanidine, tetraethoxysilane, tert-butyl lithium, trimethylacetonitrile were purchased at Sigma-Aldrich and used as purchased. Ketimines, amidines and guanidines were synthesized according to literature procedures.

Compound A: Synthesis of 1,1,1-triethoxy-N-(2,2,4,4-tetramethylpentan-3-ylidene) silanamine

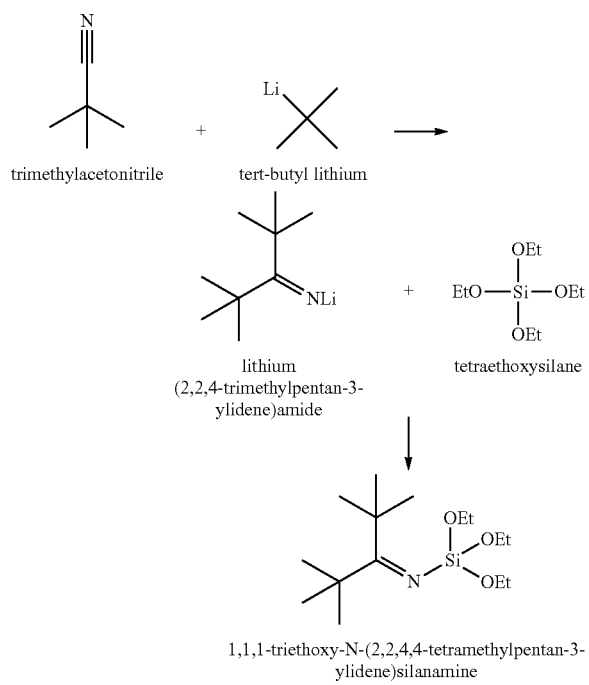

A solution of trimethylacetonitrile (7.5 g, 0.090 mol) in 150 ml n-heptane was added to a 1.3 M solution of t-butyllithium in n-pentane (91 mL, 0.81 mole) at −10° C. over 1 hr. The reaction mixture was stirred for 2 hr at 0 to −50° C. to give a pale yellow solution of lithium (2,2,4-tetramethylpentan-3-ylidene)amide. The solution was cooled to −10° C. and tetraethoxysilane (28.1 gm, 0.135 mol) was added over 15 min, while slowly rising the temperature to 10° C. The reaction mixture was quenched using 25 mL of a saturated ammonium chloride solution in water. The organic layer was separated and dried over sodium sulfate. The solvents were removed in vacuo. The remaining crude oil (16.0 g) was distilled at 120° C./2 mbar to obtain 4.9 g of 1,1,1-triethoxy-N-(2,2,4,4-tetramethylpentan-3-ylidene)silanamine (yield, 20%; purity, 93%); clear colorless liquid; GC-MS (Cl), 304.12 (m+1); $^1$H NMR (300 MHz, CDCl$_3$) δ=1.20-1.23 (t, 9H), 1.25 (d, 18H), 3.81-3.87 (q, 6H); $^{13}$C NMR (75.4 MHz, CDCl$_3$) δ=195.0, 77.3, 77.0, 76.7, 58.9, 45.3, 30.3, 18.2 ppm.

Compound B: 1,1,1-trimethoxy-N-(2,2,4,4-tetramethylpentan-3-ylidene) silanamine

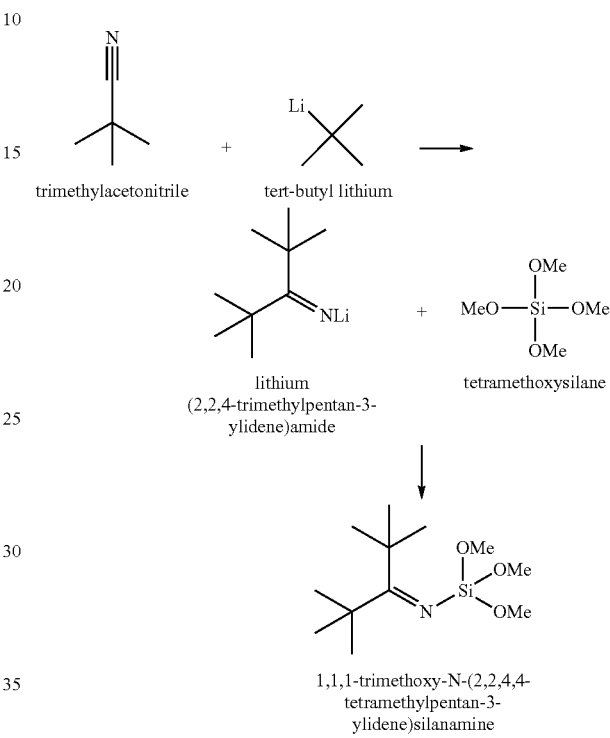

A solution of trimethylacetonitrile (7.5 g, 0.090 mole) in 150 ml n-heptane was added to a 1.3 M solution of t-butyllithium in n-pentane (100.0 mL, 0.09 mole) at −60° C. over 1 hr. The reaction mixture was stirred for 2 hr at −30 to −50° C. to give a pale yellow solution of lithium (2,2,4,4-tetramethylpentan-3-ylidene)amide. The reaction mixture was cooled to −60° C. and tetramethoxysilane (27.4 g, 0.180 mole) was added over 15 min, while slowly rising the temperature to 10° C. The reaction mixture was quenched using 25 mL of a saturated ammonium chloride solution in water. The organic layer was separated and dried over sodium sulfate. The solvents were removed in vacuo. The remaining crude oil (20.0 g) was distilled at 110° C./2 mbar to obtain 6.5 g 1,1,1-trimethoxy-N-(2,2,4,4-tetramethylpentan-3-ylidene)silanamine (yield, 27%; purity, 93.7%); clear colorless liquid; GC-MS (Cl), 261.98 (m+1), 203.92, 141.21; $^1$H NMR (400 MHz, CDCl$_3$) δ=1.24-1.27 (d, 9H), 3.59-3.60 (d, 18H); $^{13}$C NMR (100.6 MHz, CDCl$_3$) δ=196.4, 51.2, 45.5, 30.4 ppm.

Compound C: N,N,N',N'-tetramethylguanidine triethoxysilane

To a solution of N,N,N',N'-tetramethylguanidine (5.0 g, 0.043 mol) in 40 ml of hexane a 2.5 M solution of n-butyllithium (17.4 ml, 0.043 mol) was added at −78° C. A white precipitate was observed immediately upon addition. The mixture was subsequently allowed to heat up to room temperature by removing the cooling bath and stirred for an additional 30 minutes. The obtained suspension was slowly added to a solution of tetraethoxysilane (9.7 ml, 0.043 mol) in 50 ml hexane at −78° C., 40 ml of extra hexane was used to transfer the slurry to the reaction mixture. The reaction mixture was allowed to slowly heat up to room temperature and was stirred overnight. The suspension was filtered and the solvent in the obtained residue was removed under a nitrogen flow. The remaining crude oil was distilled at 130° C./0.34 mbar to obtain 8.9 g of N,N,N',N'-tetramethylguanidine triethoxysilane (yield, 74%; purity, 99+%); clear colorless liquid; $^1$H NMR (300 MHz, CDCl$_3$) δ=1.11-1.06 (t, 9H), 2.67 (s, 12H), 3.70-3.72 (q, 6H); $^{13}$C NMR (75.4 MHz, CDCl$_3$) δ=161, 59, 40, 19 ppm.

Compound D: N,N,N',N'-tetramethylguanidine trimethoxysilane

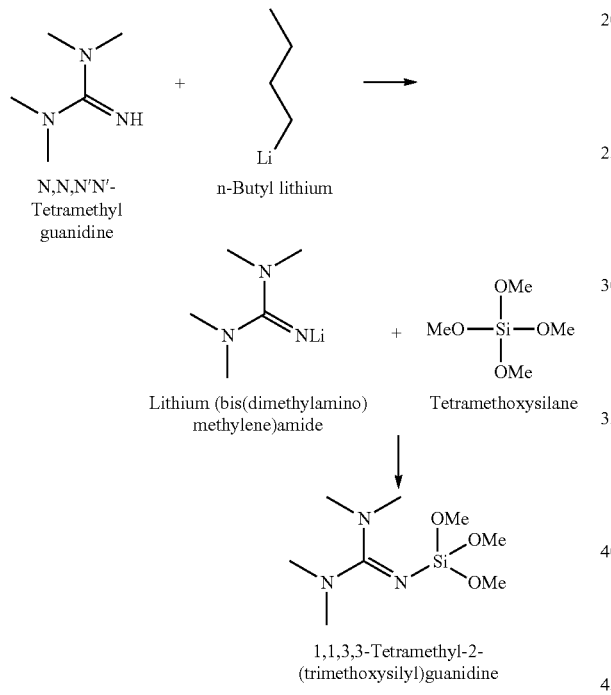

1,1,3,3-Tetramethyl-2-(trimethoxysilyl)guanidine

To a solution of N,N,N',N'-tetramethylguanidine (10.0 g, 0.087 mole) in 80 ml of hexane, a 1.6 M solution of n-butyl-lithium (54.2 ml, 0.087 mole) was added at −78° C. Immediately after addition, a white precipitate was observed. The mixture was subsequently allowed to heat up to room temperature by removing the cooling bath and stirred for an additional 30 minutes.

The obtained suspension was slowly added to a solution of tetramethoxysilane (12.8 ml, 0.087 mole) in 100 ml hexane at −78° C., 80 ml of extra hexane was used to transfer the slurry to the reaction mixture. The reaction mixture was allowed to slowly heat up to room temperature and was stirred overnight. The suspension was filtered and the solvent in the obtained residue was removed under a nitrogen flow. The remaining crude reaction mixture was distilled at 128° C./0.15 mbar to obtain 9.5 g of N,N,N',N'-tetramethylguanidine trimethoxysilane (yield, 46.5%; purity, 97+%); Pale yellow liquid; $^1$H NMR (300 MHz, CDCl$_3$) δ=2.71-2.73 (d, 12H), 3.70-3.72 (d, 9H). Anal. Calcd for C$_8$H$_{21}$N$_3$O$_3$Si (235.36): C, 40.78; H, 8.92; N, 17.84. Found: C, 39.46; H, 8.55; N, 17.455.

Compound E: Di tetramethylguanidine dimethoxysilane

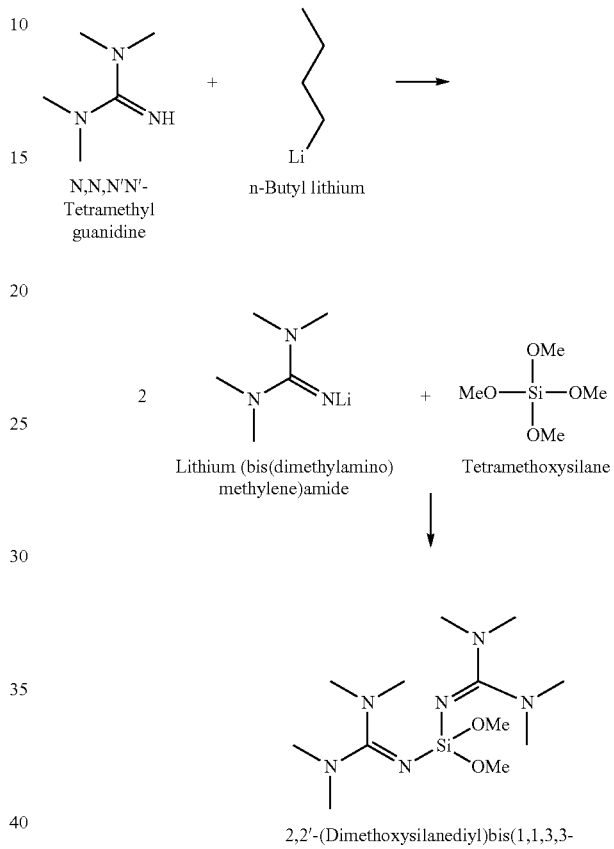

2,2'-(Dimethoxysilanediyl)bis(1,1,3,3-tetramethylguanidine)

To a solution of N,N,N',N'-tetramethylguanidine (20.0 g, 0.174 mole) in 200 ml of hexane a 1.6 M solution of n-butyl-lithium (108.5 ml, 0.174 mole) was added at −78° C. A white precipitate was observed immediately upon addition. The mixture was subsequently allowed to heat up to room temperature by removing the cooling bath and stirred for an additional 30 minutes.

The obtained suspension was slowly added to a solution of tetramethoxysilane (13.2 ml, 0.087 mole) in 200 ml hexane at −78° C., 160 ml of extra hexane was used to transfer the slurry to the reaction mixture. The reaction mixture was allowed to slowly heat up to room temperature and was stirred for 16 h. The suspension was filtered and the solvent in the obtained residue was removed under a nitrogen flow. The remaining crude reaction mixture was distilled at 135° C./0.2 mbar to obtain 10.3 g of Di tetramethylguanidine dimethoxysilane (yield, 18.7%; purity, 95+%); clear colorless liquid; $^1$H NMR (300 MHz, CDCl$_3$) δ=2.677-2.679 (d, 24H), 3.542-3.544 (d, 6H). Anal. Calcd for C$_{12}$H$_{30}$N$_6$O$_2$Si (318.5): C, 45.25; H, 9.49; N, 26.38. Found: C, 44.87; H, 10.02; N, 25.12.

Compound F: Tetra tetramethylguanidine silane

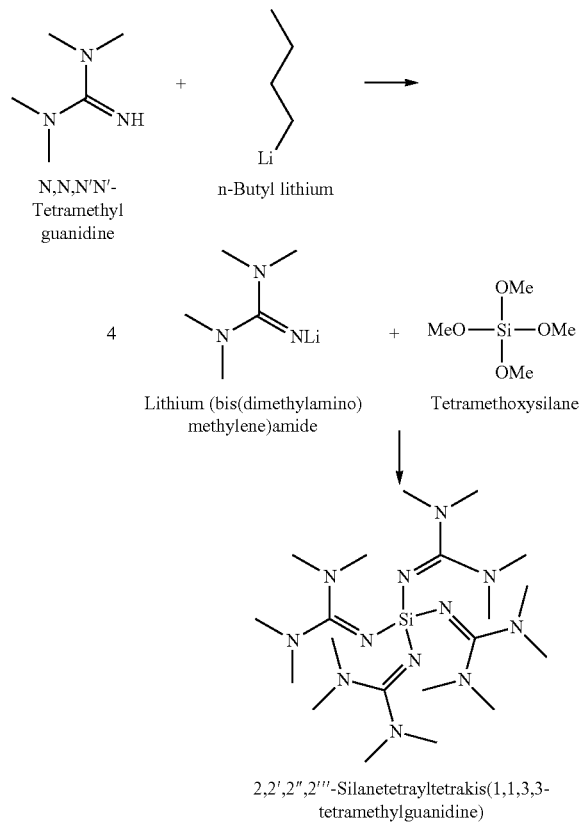

2,2′,2″,2‴-Silanetetrayltetrakis(1,1,3,3-tetramethylguanidine)

To a solution of N,N,N',N'-tetramethylguanidine (10.0 g, 0.087 mol) in 100 ml of hexane a 1.6 M solution of n-butyl-lithium (59.0 ml, 0.087 mol) was added at −78° C. A white precipitate was observed immediately upon addition. The mixture was subsequently allowed to heat up to room temperature by removing the cooling bath and stirred for an additional 30 minutes.

The obtained suspension was slowly added to a solution of tetramethoxysilane (2.52 ml, 0.017 mol) in 100 ml hexane at −78° C., 100 ml of extra hexane was used to transfer the slurry to the reaction mixture. The reaction mixture was allowed to slowly heat up to room temperature and was stirred for 24 h. The suspension was filtered and the solvent in the obtained residue was removed under a nitrogen flow. The remaining crude reaction mixture was distilled at 100° C./0.25 mbar to obtain 10.8 g of Tetra tetramethylguanidine silane (yield, 26.4%; purity, 95+%); clear colorless liquid; $^1$H NMR (300 MHz, CDCl$_3$) δ=2.69-2.70 (d, 48H). Anal. Calcd for C$_{19}$H$_{45}$N$_{12}$Si (469.74): C, 49.55; H, 9.98; N, 34.67. Found: C, 48.43; H, 10.95; N, 33.075.

Synthesis of the Procatalyst Component

A. Grignard Formation Step (Step o))

A stirred flask, fitted with a reflux condenser and a funnel, was filled with magnesium powder (24.3 g). The flask was brought under nitrogen. The magnesium was heated at 80° C. for 1 hour, after which dibutyl ether (DBE, 150 ml), iodine (0.03 g) and n-chlorobutane (4 ml) were successively added. After the colour of the iodine had disappeared, the temperature was raised to 80° C. and a mixture of n-chlorobutane (110 ml) and dibutyl ether (750 ml) was slowly added for 2.5 hours. The reaction mixture was stirred for another 3 hours at 80° C. Then the stirring and heating were stopped and the small amount of solid material was allowed to settle for 24 hours. By decanting the colorless solution above the precipitate, a solution of butylmagnesiumchloride (reaction product of step A) with a concentration of 1.0 mol Mg/l was obtained.

B. Preparation of the Intermediate Reaction Product (Step i))

250 mL of dibutyl ether was introduced to a 1 L reactor fitted with a propeller stirrer and two baffles. The reactor was thermostated at 35° C. and the stirrer speed was kept at 200 rpm. Then a cooled (to 15° C.) 360 mL solution of the Grignard reaction product as prepared in A and 180 ml of a cooled (to 15° C.) solution of tetraethoxysilane (TES) in dibutyl ether (consisting of 38 ml of TES and 142 ml of DBE) were dosed into the reactor for 400 min. with preliminary mixing in a minimixer of 0.15 ml volume, which was cooled to 15° C. by means of cold water circulating in the minimixer jacket. The premixing time was 18 seconds in the minimixer and the connecting tube between the minimixer and the reactor. The stirring speed in the minimixer was 1000 rpm. On the dosing completion, the reaction mixture was kept at 35° C. for 0.5 hours. Then the reactor was heated to 60° C. and kept at this temperature for 1 hour. Then the stirrer was stopped and the solid substance was allowed to settle. The supernatant was removed by decanting. The solid substance was washed three times using 300 ml of heptane. As a result, a white solid reaction product was obtained and suspended in 200 ml of heptane.

Under an inert nitrogen atmosphere at 20° C. a 250 ml glass flask equipped with a mechanical agitator is filled with a slurry of 5 g of the reaction product of step B dispersed in 60 ml of heptane. Subsequently a solution of 0.86 ml methanol (MeOH/Mg=0.5 mol) in 20 ml heptane is dosed under stirring during 1 hour. After keeping the reaction mixture at 20° C. for 30 minutes the slurry was slowly allowed to warm up to 30° C. for 30 min and kept at that temperature for another 2 hours. Finally the supernatant liquid is decanted from the solid reaction product which was washed once with 90 ml of heptane at 30° C.

C. Preparation of the Procatalyst Component (Phase C)

A reactor was brought under nitrogen and 125 ml of titanium tetrachloride was added to it. The reactor was heated to 90° C. and a suspension, containing about 5.5 g of the support obtained in step C in 15 ml of heptane, was added to it under stirring. The reaction mixture was kept at 90° C. for 10 min. Then ethyl benzoate was added (EB/Mg=0.15 molar ratio). The reaction mixture was kept for 60 min. Then the stirring was stopped and the solid substance was allowed to settle. The supernatant was removed by decanting, after which the solid product was washed with chlorobenzene (125 ml) at 90° C. for 20 min. The washing solution was removed by decanting, after which a mixture of titanium tetrachloride (62.5 ml) and chlorobenzene (62.5 ml) was added. The reaction mixture was kept at 90° C. for 30 min. After which the stirring was stopped and the solid substance was allowed to settle. The supernatant was removed by decanting, after which a mixture of titanium tetrachloride (62.5 ml) and chlorobenzene (62.5 ml) was added. Then di-n-butyl phthalate (DNB) (DNB/Mg=0.15 molar ratio) in 3 ml of chlorobenzene was added to reactor and the temperature of reaction mixture was increased to 115° C. The reaction mixture was kept at 115° C. for 30 min. After which the stirring was stopped and the solid substance was allowed to settle. The supernatant was removed by decanting, after which a mixture of titanium tetrachloride (62.5 ml) and chlorobenzene (62.5 ml) was added. The reaction mixture was kept at 115° C. for 30 min, after which the solid substance was allowed to settle. The supernatant was removed by decanting and the solid was washed five times using 150 ml of heptane at 60° C., after which the procatalyst component, suspended in heptane, was obtained.

Propylene-ethylene co-polymerization

All polymerization experiments were performed using a magnesium/titanium/chloride containing catalyst which was prepared according to EP1838741B.

The copolymerization of propylene and ethylene was carried out in a stainless steel reactor with a volume of 1800 mL. The co-catalyst (TEAL) and procatalyst component synthesised according to the procedure described above (steps A to C) and the external electron donor were dosed as heptane solutions or slurries to the reactor (Al/Titanium molar ratio=50 and Si/Ti ratio=4.5), which is under a nitrogen atmosphere, while the reactor temperature is maintained below 30° C. Subsequently, the reactor was pressurized using a set ratio of propylene, ethylene and hydrogen, and the temperature and pressure were raised to its setpoint (60° C. and 20 barg). After the pressure setpoint has been reached, the polymerization was continued for 75 minutes. During the polymerization reaction the gas cap composition of propylene, ethylene and hydrogen was controlled using mass flow meters and online-GC control. After reaching the polymerization time the reactor was depressurized and cooled to ambient conditions. The propylene-ethylene random copolymer so obtained was removed from the reactor and stored in aluminium bags.

Polymer Analysis

Polymer yield is expressed as total mass of polymer isolated from the reactor.

Catalyst yield is expressed as kilogram of polymer isolated per gram of catalyst after the 75 minutes of polymerization time.

$H_2/C_3$ is the percentage of hydrogen over propylene in the gas cap of the reactor.

$C_2/C_3$ is the percentage of ethylene over propylene in the gas cap of the reactor.

Results of the Polymerization Experiments

The following propylene-ethylene co-polymerization experiments were performed using the above reactor conditions. In a reference experiment a standard external donor was used, being diisobutyl dimethoxysilane (DIBDMS); this is comparative example C1. For Example 1 Compound A prepared as discussed above was used. For Example 2 Compound B prepared as discussed above was used. For Example 3 Compound C prepared as discussed above was used. For Example 4 Compound D prepared as discussed above was used. For Example 5 Compound E prepared as discussed above was used. For Example 6 Compound F prepared as discussed above was used.

Compound A=Si(L)(OEt)$_3$ wherein L=N-(2,2,4,4-tetramethylpentan-3-ylidene)

Compound B=Si(L)(OMe)$_3$ wherein L=N-(2,2,4,4-tetramethylpentan-3-ylidene)

Compound C=Si(L)(OEt)$_3$ wherein L=N,N,N',N'-tetramethylguanidine

Compound D=Si(L)(OMe)$_3$ wherein L=N,N,N',N'-tetramethylguanidine

Compound E=Si(L)$_2$(OMe)$_2$ wherein L=N,N,N',N'-tetramethylguanidine

Compound F=Si(L)$_4$ wherein L=N,N,N',N'-tetramethylguanidine

The difference between compound A and compound B is in the OR groups wherein for compound A R is ethyl and for compound B R is methyl.

The difference between compound C and compound D is in the OR groups wherein for compound C R is ethyl and for compound D R is methyl.

The difference between compound A and compound C is in the L group wherein for compound A L is N-(2,2,4,4-tetramethylpentan-3-ylidene) and for compound C L is N,N,N',N'-tetramethylguanidine.

The difference between compound B and compound D is in the L group wherein for compound B L is N-(2,2,4,4-tetramethylpentan-3-ylidene) and for compound D L is N,N,N',N'-tetramethylguanidine.

The difference between compounds D, E and F is that compound F has four L groups, compound E has two L groups whereas compound D has one L group.

From the table below it is clear that with all of the compounds according to the present invention, compared with the comparative example, the lump content is remarkable decreased from 28.7 of the comparative example (C1) to a value between 2.8 and 11.7 for Examples 1-5.

Furthermore, one can for example see from the comparison between the compounds C to F on one hand as well as A and B on the other hand, that depending on the L group, the number and/or bulk/length of the OR can either decrease or increase the lump formation as well as the yield.

For the compounds C to F, one sees that decreasing the number and/or the bulk/length of the OR group(s) tends to decrease the tendency to form lumps formation. However, for Compound F it was not possible to measure the actual lump content because of the formation of one big viscous mass (a big lump). Moreover, decreasing the hinderance arising for example from bulky groups around the Si increases yield. Compound D thereby for example combines a good yield with a low tendency to lump formation In contrast, for the compounds A and B, with another L group, one sees that increasing the number and/or the bulk/length of the OR group(s) decreases lump formation here. Yield increases again when hinderance arising for example from bulky groups around the Si is decreased.

Especially, compounds A and B thereby showed excellent yields together with a low tendency to form lumps.

This is accordingly an exemplary way that one can tune for example the tendency to form lumps and/or the yield.

The results are shown in Table 1.

TABLE 1

| Exp. | External donor | H$_2$/C$_3$ vol. % | C$_2$/C$_3$ vol. % | Polymer yield (gram) | Catalyst yield Kg/g | MFR g/10 min | C2 content wt. % | Lump content wt. % | XS wt % |
|---|---|---|---|---|---|---|---|---|---|
| C1 | DIBDMS | 5.1 | 1.9 | 188 | 22.6 | 22.61 | 8.6 | 28.7 | 10.6 |
| 1 | Compound A | 3.1 | 1.7 | 311 | 20.7 | 23.8 | 4.2 | 2.8 | 11.7 |
| 2 | Compound B | 3.2 | 1.7 | 378 | 25.3 | 16.1 | 7.1 | 9.0 | 7.6 |
| 3 | Compound C | 5.0 | 2.8 | 60 | 4.0 | 52.3 | 5.6 | 11.7 | 22.2 |
| 4 | Compound D | 4.7 | 2.2 | 203 | 13.5 | 18.9 | 4.8 | 4.4 | 16.7 |
| 5 | Compound E | 5.0 | 2.2 | 150 | 10.0 | 28.9 | 5.1 | 4.0 | 21.1 |
| 6 | Compound F | 4.9 | 2.0 | 75 | 5.0 | 75.7 | 5.8 | not measured | 27.5 |

The invention claimed is:

1. A catalyst system suitable for olefin polymerization comprising a Ziegler-Natta type procatalyst, a co-catalyst and at least one external electron donor, wherein the external electron donor comprises a compound having the structure according to Formula I:

$$Si(L)_n(OR^{11})_{4-n} \quad \text{(Formula I)},$$

wherein,
Si is a silicon atom with valency 4+;
O is an oxygen atom with valency 2- and O is bonded to Si via a silicon-oxygen bond;
n is 1, 2, 3 or 4;
R$^{11}$ is a selected from the group consisting of linear, branched and cyclic alkyl having at most 20 carbon atoms and aromatic substituted and unsubstituted hydrocarbyl having 6 to 20 carbon atoms;
L is a group represented by the following structure

wherein,
L is bonded to the silicon atom via a nitrogen-silicon bond;
L has a single substituent on the nitrogen atom, where this single substituent is an imine carbon atom; and
X and Y are each independently selected from the group consisting of:
a) a hydrogen atom;
b) a group comprising a heteroatom selected from group 13, 14, 15, 16 or 17 of the IUPAC Periodic Table of the Elements through which X and Y are each independently bonded to the imine carbon atom of Formula II, wherein the heteroatom is substituted with a group consisting of a linear, branched and cyclic alkyl groups having at most 20 carbon atoms, optionally containing a heteroatom selected from group 13, 14, 15, 16 or 17 of the IUPAC Periodic Table of the Elements; and/or with an aromatic substituted and unsubstituted hydrocarbyl groups having 6 to 20 carbon atoms, optionally containing a heteroatom selected from group 13, 14, 15, 16 or 17 of the IUPAC Periodic Table of the Elements;
c) a linear, branched and cyclic alkyl having at most 20 carbon atoms, optionally containing a heteroatom selected from group 13, 14, 15, 16 or 17 of the IUPAC Periodic Table of the Elements; and
d) an aromatic substituted and unsubstituted hydrocarbyl having 6 to 20 carbon atoms, optionally containing a heteroatom selected from group 13, 14, 15, 16 or 17 of the IUPAC Periodic Table of the Elements.

2. The catalyst system according to claim 1, wherein L is guanidine, amidine or ketimide.

3. The catalyst system according to claim 1, wherein R$^{11}$ is an alkyl having at most 10 carbon atoms.

4. A process for preparing the catalyst system according to claim 1, comprising contacting a Ziegler-Natta type procatalyst, a co-catalyst and at least one external electron donor comprising the compound according to Formula I.

5. The process according to claim 4, said process comprising the steps of:
A) providing a Ziegler-Natta procatalyst obtained via a process comprising the steps of:
i) contacting a compound R$^4_z$MgX$^4_{2-z}$ with an alkoxy- or aryloxy-containing silane compound to give a first intermediate reaction product, being a solid Mg(OR$^1$)$_x$X$^1_{2-x}$, wherein: R$^4$ is the same as R$^1$ being a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms and preferably has from 1 to 20 carbon atoms; X$^4$ and X$^1$ are each independently selected from the group consisting of fluoride (F—), chloride (Cl—), bromide (Br—) or iodide (I—), preferably chloride; z is in a range of larger than 0 and smaller than 2, being 0<z<2;
ii) optionally contacting the solid Mg(OR$^1$)$_x$X$^1_{2-x}$ obtained in step ii) with at least one activating compound selected from the group formed of activating electron donors and metal alkoxide compounds of formula M$^1$(OR$^2$)$_{v-w}$(OR$^3$)$_w$ or M$^2$(OR$^2$)$_{v-w}$(R$^3$)$_w$, to obtain a second intermediate product; wherein M$^1$ is a metal selected from the group consisting of Ti, Zr, Hf, Al or Si; M$^2$ is a metal being Si; v is the valency of M$^1$ or M$^2$; R$^2$ and R$^3$ are each a linear, branched or cyclic hydrocarbyl group independently selected from alkyl, alkenyl, aryl, aralkyl, alkoxycarbonyl or alkylaryl groups, and one or more combinations thereof; wherein said hydrocarbyl group may be substituted or unsubstituted, may contain one or more heteroatoms, and preferably has from 1 to 20 carbon atoms;
iii) contacting the first or second intermediate reaction product, obtained respectively in step i) or ii), with a halogen-containing Ti-compound and optionally an internal electron donor to obtain said procatalyst;

B) contacting said procatalyst with a co-catalyst and at least one external electron donor being a compound having the structure according to Formula I.

6. The process according to claim 5, wherein $Mg(OR^1)_xX^1_{2-x}$ is contacted in step ii) with titanium tetraalkoxide and an alcohol as activating compounds.

7. The process according to claim 4, wherein the co-catalyst is a hydrocarbyl aluminum compound represented by the formula $R^{21}_mAlX^{21}_{3-m}$ wherein m=1 or 2, R is an alkyl, and X is a halide or alkoxide.

8. A process for preparing a polyolefin by contacting at least one olefin with the catalyst system according to claim 1.

9. The process according to claim 8, wherein the at least one olefin is propylene or a mixture of propylene and ethylene.

10. A method for the polymerization of an olefin, comprising:
   polymerizing the olefin using the compound having the structure according to Formula I according to claim 1 as an external electron donor in a Ziegler-Natta type catalyst system.

* * * * *